US010206990B2

(12) United States Patent
Philip

(10) Patent No.: US 10,206,990 B2
(45) Date of Patent: Feb. 19, 2019

(54) CYTOTOXIC T LYMPHOCYTE INDUCING IMMUNOGENS FOR PREVENTION TREATMENT AND DIAGNOSIS OF CANCER

(71) Applicant: Immunotope, Inc., Doylestown, PA (US)

(72) Inventor: Ramila Philip, Ivyland, PA (US)

(73) Assignee: Immunotope, Inc., Doylestown, PA (US)

( * ) Notice: Subject to any disclaimer, the term of this patent is extended or adjusted under 35 U.S.C. 154(b) by 0 days.

(21) Appl. No.: 15/447,598

(22) Filed: Mar. 2, 2017

(65) Prior Publication Data
US 2017/0173135 A1 Jun. 22, 2017

Related U.S. Application Data

(62) Division of application No. 14/344,048, filed as application No. PCT/US2012/054826 on Sep. 12, 2012, now Pat. No. 9,624,284.

(60) Provisional application No. 61/533,852, filed on Sep. 13, 2011, provisional application No. 61/611,725, filed on Mar. 16, 2012.

(51) Int. Cl.
*A61K 38/00* (2006.01)
*A61K 39/00* (2006.01)
*C07K 14/74* (2006.01)
*A61K 38/19* (2006.01)
*A61K 38/20* (2006.01)
*C07K 7/06* (2006.01)
*C07K 14/47* (2006.01)

(52) U.S. Cl.
CPC ........ *A61K 39/0011* (2013.01); *A61K 38/191* (2013.01); *A61K 38/193* (2013.01); *A61K 38/2006* (2013.01); *A61K 38/208* (2013.01); *A61K 38/2013* (2013.01); *A61K 38/2046* (2013.01); *A61K 38/2086* (2013.01); *C07K 7/06* (2013.01); *C07K 14/4748* (2013.01); *C07K 14/70539* (2013.01); *A61K 2039/55566* (2013.01); *A61K 2039/572* (2013.01)

(58) Field of Classification Search
None
See application file for complete search history.

(56) References Cited

U.S. PATENT DOCUMENTS

| | | |
|---|---|---|
| 4,235,871 A | 11/1980 | Szoka et al. |
| 4,501,728 A | 2/1985 | Geho et al. |
| 4,690,915 A | 9/1987 | Rosenberg |
| 4,722,848 A | 2/1988 | Paoletti et al. |
| 4,837,028 A | 6/1989 | Allen |
| 4,844,893 A | 7/1989 | Honsik et al. |
| 5,019,369 A | 5/1991 | Presant et al. |
| 5,635,363 A | 6/1997 | Altman et al. |

| | | | |
|---|---|---|---|
| 2007/0048301 A1* | 3/2007 | Bodary-Winter | ...... C07K 14/47 424/143.1 |
| 2008/0107668 A1 | 5/2008 | Philip et al. | |
| 2012/0141579 A1 | 6/2012 | Philip | |
| 2014/0105925 A1 | 4/2014 | Philip | |

OTHER PUBLICATIONS

Slovin SF, Lackman RD, Ferrone S, Kiely PE, Mastraugelo MJ. Cellular immune response to human sarcomas: cytotoxic T cell clones reactive with autologous sarcomas. I. Development, phenotype, and specificity. J Immunol. 1986;137(9):3042-8. Epub Nov. 1, 1986. PubMed PMID: 3093588.
Schendel DJ, Gansbacher B, Oberneder R, Knegmair M, Hofstetter A, Riethmuller G, et al. Tumor-specific lysis of human renal cell carcinomas by tumor-infiltrating lymphocytes. I. HLA-A2-restricted recognition of autologous and allogeneic tumor lines. J Immunol. 1993;151(8):4209-20. Epub Oct. 15, 1993. PubMed PMID: 8409397.
Jacob L, Somasundaram R, Smith W, Monos D, Basak S, Marincola F, et al. Cytotoxic T-cell clone against rectal carcinoma induced by stimulation of a patient's peripheral blood mononuclear cells with autologous cultured tumor cells. Int J Cancer. 1997;71(3):325-32. Epub May 2, 1997. PubMed PMID: 9139862.
Ioannides CG, Freedman RS, Platsoucas CD, Rashed S, Kim YP. Cytotoxic T cell clones isolated from ovarian tumor-infiltrating lymphocytes recognize multiple antigenic epitopes on autologous tumor cells. J Immunol. 1991;146(5):1700-7. Epub Mar. 1, 1991. PubMed PMID: 1704404.
Peoples GE, Schoof DD, Andrews JV, Goedegebuure PS, Eberlein TJ. T-cell recognition of ovarian cancer. Surgery. 1993;114(2):227-34. Epub Aug. 1, 1993. PubMed PMID: 8342128.
Peiper M, Goedegebuure PS, Linehan DC, Ganguly E, Douville CC, Eberlein TJ. The HER2/neu-derived peptide p654-662 is a tumor-associated antigen in human pancreatic cancer recognized by cytotoxic T lymphocytes. Eur J Immunol. 1997;27(5):1115-23. Epub May 1, 1997. doi: 10.1002/eji.1830270511. PubMed PMID: 9174600.
Wolfel T, Herr W, Coulie P, Schmitt U, Meyer Zum Buschenfelde KH, Knuth A. Lysis of human pancreatic adenocarcinoma cells by autologous HLA-class I-restricted cytolytic T-lymphocyte (CTL) clones. Int J Cancer. 1993;54(4):636-44. Epub Jun. 19, 1993. PubMed PMID: 8514455.
Yasumura S, Hirabayashi H, Schwartz DR, Toso JF, Johnson JT, Herberman RB, et al. Human cytotoxic T-cell lines with restricted specificity for squamous cell carcinoma of the head and neck. Cancer Res. 1993;53(6):1461-8. Epub Mar. 15, 1993. PubMed PMID: 8443824.
Slingluff CL, Jr., Cox AL, Stover JM, Jr., Moore MM, Hunt DF, Engelhard VH. Cytotoxic T-lymphocyte response to autologous human squamous cell cancer of the lung: epitope reconstitution with peptides extracted from HLA-Aw68. Cancer Res. 1994;54(10):2731-7. Epub May 15, 1994. PubMed PMID: 7513255.

(Continued)

*Primary Examiner* — Jeanette M Lieb
(74) *Attorney, Agent, or Firm* — Joseph F. Aceto, Esq.

(57) ABSTRACT

The present invention relates to compositions and methods for the prevention, treatment, and diagnosis of cancer, especially carcinomas, such as pancreatic carcinoma. The invention discloses peptides, polypeptides, and polynucleotides that can be used to stimulate a CTL response against pancreatic and other cancers.

8 Claims, 2 Drawing Sheets
Specification includes a Sequence Listing.

(56) References Cited

OTHER PUBLICATIONS

Yoshino I, Goedegebuure PS, Peoples GE, Parikh AS, DiMaio JM, Lyerly HK, et al. HER2/neu-derived peptides are shared antigens among human non-small cell lung cancer and ovarian cancer. Cancer Res. 1994;54(13):3387-90. Epub Jul. 1, 1994. PubMed PMID: 7912166.

Boon T, Cerottini JC, Van Den Eynde B, Van Der Bruggen P, Vanpela. Tumor antigens recognized by T lymphocytes. Annu Rev Immunol. 1994;12:337-65. Epub Jan. 1, 1994. doi: 10.1146/annurev. iy.12.040194.002005. PubMed PMID: 8011285.

Rosenberg SA, Packard BS, Aebersold PM, Solomon D, Topalian SL, Toy ST, et al. Use of tumor-infiltrating lymphocytes and interleukin-2 in the immunotherapy of patients with metastatic melanoma. A preliminary report. N Engl J Med. 1988;319(25):1676-80. Epub Dec. 22, 1988. doi: 10.1056/NEJM198812223192527. PubMed PMID: 3264384.

Celluzzi CM, Mayordomo JI, Storkus WJ, Lotze MT, Falo LD, Jr. Peptide-pulsed dendritic cells induce antigen-specific CTL-mediated protective tumor immunity. J Exp Med. 1996;183(1):283-7. Epub Jan. 1, 1996. PubMed PMID: 8551233; PubMed Central PMCID: PMC2192396.

Mayordomo JI, Zorina T, Storkus WJ, Zitvogel L, Celluzzi C, Falo LD, et al. Bone marrow-derived dendritic cells pulsed with synthetic tumour peptides elicit protective and therapeutic antitumour immunity. Nat Med. 1995;1(12):1297-302. Epub Dec. 1, 1995. PubMed PMID: 7489412.

Zitvogel L, Mayordomo JI, Tjandrawan T, DeLeo AB, Clarke MR, Lotze MT, et al. Therapy of murine tumors with tumor peptide-pulsed dendritic cells: dependence on T cells, B7 costimulation, and T helper cell 1-associated cytokines. J Exp Med. 1996;183(1):87-97. Epub Jan. 1, 1996. PubMed PMID: 8551248; PubMed Central PMCID: PMC2192415.

Rock KL, Goldberg AL. Degradation of cell proteins and the generation of MHC class I-presented peptides. Annu Rev Immunol. 1999;17:739-79. Epub Jun. 8, 1999. doi: 10.1146/annurev.immunol. 17.1.739. PubMed PMID: 10358773.

Watts C. Capture and processing of exogenous antigens for presentation on MHC molecules. Annu Rev Immunol. 1997;15:821-50. Epub Jan. 1, 1997. doi: 10.1146/annurev.immunol.15.1.821. PubMed PMID: 9143708.

Rosenberg SA. A new era for cancer immunotherapy based on the genes that encode cancer antigens. Immunity. 1999;10(3):281-7. Epub Apr. 16, 1999. PubMed PMID: 10204484.

Gilboa E. The makings of a tumor rejection antigen. Immunity. 1999;11(3):263-70. Epub Oct. 8, 1999. PubMed PMID: 10514004.

Yewdell JW, Bennink JR. Mechanisms of viral interference with MHC class I antigen processing and presentation. Annual review of cell and developmental biology. 1999;15:579-606. Epub Dec. 28, 1999. doi: 10.1146/annurev.cellbio.15.1.579. PubMed PMID: 10611973.

Henderson RA, Cox AL, Sakaguchi K, Appella E, Shabanowitz J, Hunt DF, et al. Direct identification of an endogenous peptide recognized by multiple HLA-A2.1-specific cytotoxic T cells. Proc Natl Acad Sci U S A. 1993;90(21):10275-9. Epub Nov. 1, 1993. PubMed PMID: 7694286; PubMed Central PMCID: PMC47757.

Hogan KT, Eisinger DP, Cupp SB, 3rd, Lekstrom KJ, Deacon DD, Shabanowitz J, et al. The peptide recognized by HLA-A68.2-restricted, squamous cell carcinoma of the lung-specific cytotoxic T lymphocytes is derived from a mutated elongation factor 2 gene. Cancer Res. 1998;58(22):5144-50. Epub Nov. 21, 1998. PubMed PMID: 9823325.

Hunt DF, Henderson RA, Shabanowitz J, Sakaguchi K, Michel H, Sevilir N, et al. Characterization of peptides bound to the class I MHC molecule HLA-A2.1 by mass spectrometry. Science. 1992;255(5049):1261-3. Epub Mar. 6, 1992. PubMed PMID: 1546328.

Slingluff CL, Jr., Cox AL, Henderson RA, Hunt DF, Engelhard VH. Recognition of human melanoma cells by HLA-A2.1-restricted cytotoxic T lymphocytes is mediated by at least six shared peptide epitopes. J Immunol. 1993;150(7):2955-63. Epub Apr. 1, 1993. PubMed PMID: 7681084.

Grant GA. Synthetic Peptides: A User's Guide. New York: W. H. Freeman and Company; 1992.

Coligan JE. Current Protocols in Protein Science. New York: John Wiley & Sons, Inc.; 1999.

Ausubel FM. Current Protocols in Molecular Biology. New York: John Wiley & Sons, Inc.; 1999.

Molecular Cloning: A Laboratory Manual. Cold Spring Harbor: Cold Spring Harbor Laboratory Press; 1989.

Posnett DN, McGrath H, Tam JP. A novel method for producing anti-peptide antibodies. Production of site-specific antibodies to the T cell antigen receptor beta-chain. J Biol Chem. 1988;263(4):1719-25. Epub Feb. 5, 1988. PubMed PMID: 3276675.

Parkhurst MR, Salgaller ML, Southwood S, Robbins PF, Setto A, Rosenberg SA, et al. Improved induction of melanoma-reactive CTL with peptides from the melanoma antigen gp100 modified at HLA-A*0201-binding residues. J Immunol. 1996;157(6):2539-48. Epub Sep. 15, 1996. PubMed PMID: 8805655.

Rosenberg SA, Yang JC, Schwartzentruber DJ, Hwu P, Marincola FM, Topalian SL, et al. Immunologic and therapeutic evaluation of a synthetic peptide vaccine for the treatment of patients with metastatic melanoma. Nat Med. 1998;4(3):321-7. Epub Mar. 21, 1998. PubMed PMID: 9500606; PubMed Central PMCID: PMC2064864.

Gluzman Y. SV40-transformed simian cells support the replication of early SV40 mutants. Cell. 1981;23(1):175-82. Epub Jan. 1, 1981. PubMed PMID: 6260373.

Ljunggren HG, Stam NJ, Ohlen C, Neefjes JJ, Hoglund P, Heemels MT, et al. Empty MHC class I molecules come out in the cold. Nature. 1990;346(6283):476-80. Epub Aug. 2, 1990. doi: 10.1038/346476a0. PubMed PMID: 2198471.

Zen HJ, 3rd, Leder GH, Lotze MT, Salter RD, Tector M, Stuber G, et al. Flow-cytometric determination of peptide-class I complex formation. Identification of p53 peptides that bind to HLA-A2. Hum Immunol. 1994;39(2):79-86. Epub Feb. 1, 1994. PubMed PMID: 8175386.

Riddell SR, Greenberg PD. The use of anti-CD3 and anti-CD28 monoclonal antibodies to clone and expand human antigen-specific T cells. J Immunol Methods. 1990;128(2):189-201. Epub Apr. 17, 1990. PubMed PMID: 1691237.

Walter EA, Greenberg PD, Gilbert MJ, Finch RJ, Watanabe KS, Thomas ED, et al. Reconstitution of cellular immunity against cytomegalovirus in recipients of allogeneic bone marrow by transfer of T-cell clones from the donor. N Engl J Med. 1995;333(16):1038-44. Epub Oct. 19, 1995. doi: 10.1056/NEJM199510193331603. PubMed PMID: 7675046.

Harding CV, 3rd. Electroporation of exogenous antigen into the cytosol for antigen processing and class I major histocompatibility complex (MHC) presentation: weak base amines and hypothermia (18 degrees C) inhibit the class I MHC processing pathway. Eur J Immunol. 1992;22(7):1865-9. Epub Jul. 1, 1992. doi: 10.1002/eji. 1830220728. PubMed PMID: 1623927.

Reddy R, Zhou F, Huang L, Carbone F, Bevan M, Rouse BT. pH sensitive liposomes provide an efficient means of sensitizing target cells to class I restricted CTL recognition of a soluble protein. J Immunol Methods. 1991;141(2):157-63. Epub Aug. 9, 1991. PubMed PMID: 1880423.

Moore MW, Carbone FR, Bevan MJ. Introduction of soluble protein into the class I pathway of antigen processing and presentation. Cell. 1988;54(6):777-85. Epub Sep. 9, 1988 PubMed PMID: 3261634.

Tuting T, Wilson CC, Martin DM, Kasamon YL, Rowles J, Ma DI, et al. Autologous human monocyte-derived dendritic cells genetically modified to express melanoma antigens elicit primary cytotoxic T cell responses in vitro: enhancement by cotransfection of genes encoding the Th1-biasing cytokines IL-12 and IFN-alpha. J Immunol. 1998;160(3):1139-47. Epub May 7, 1998. PubMed PMID: 9570527.

Perez-Diez A, Butterfield LH, Li L, Chakraborty NG, Economou JS, Mukherji B. Generation of CD8+ and CD4+ T-cell response to dendritic cells genetically engineered to express the MART-1/Melan-A gene. Cancer Res. 1998;58(23):5305-9. Epub Dec. 16, 1998. PubMed PMID: 9850054.

North RJ, LaCourse R, Ryan L. Vaccinated mice remain more susceptible to *Mycobacterium tuberculosis* infection initiated via the respiratory route than via the intravenous route. Infect Immun.

(56) References Cited

OTHER PUBLICATIONS

1999;67(4):2010-2. Epub Mar. 20, 1999. PubMed PMID: 10085050; PubMed Central PMCID: PMC96560.

Riddell SR, Watanabe KS, Goodrich JM, Li CR, Agha ME, Greenberg PD. Restoration of viral immunity in immunodeficient humans by the adoptive transfer of T cell clones. Science. 1992;257(5067):238-41. Epub Jul. 10, 1992. PubMed PMID: 1352912.

Ramakrishna V, Ross MM, Pettersson M, Gatlin CC, Lyons CE, Miller CL, et al. Naturally occurring peptides associated with HLA-A2 in ovarian cancer cell lines identified by mass spectrometry are targets of HLA-A2-restricted cytotoxic T cells. Int Immunol. 2003;15(6):751-63. Epub May 17, 2003. PubMed PMID: 12750359.

Morse MA, Nair SK, Mosca PJ, Hobeika AC, Clay TM, Deng Y, et al. Immunotherapy with autologous, human dendritic cells transfected with carcinoembryonic antigen mRNA. Cancer Invest. 2003;21(3):341-9. Epub Aug. 7, 2003. PubMed PMID: 12901279.

Hanahan D, Weinberg RA. The hallmarks of cancer. Cell. 2000;100(1):57-70. Epub Jan. 27, 2000. PubMed PMID: 10647931.

* cited by examiner

Figure 1: In vitro characterization of cancer epitopes.

Figure 2
Panel A
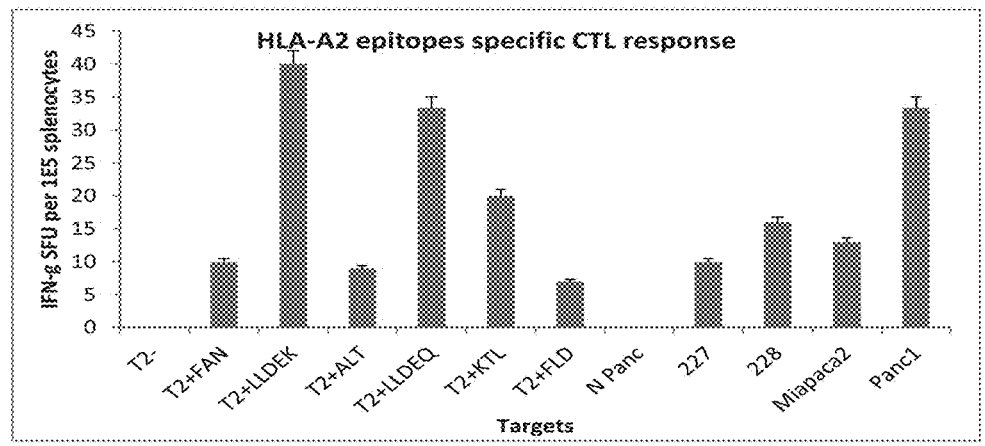
Panel B
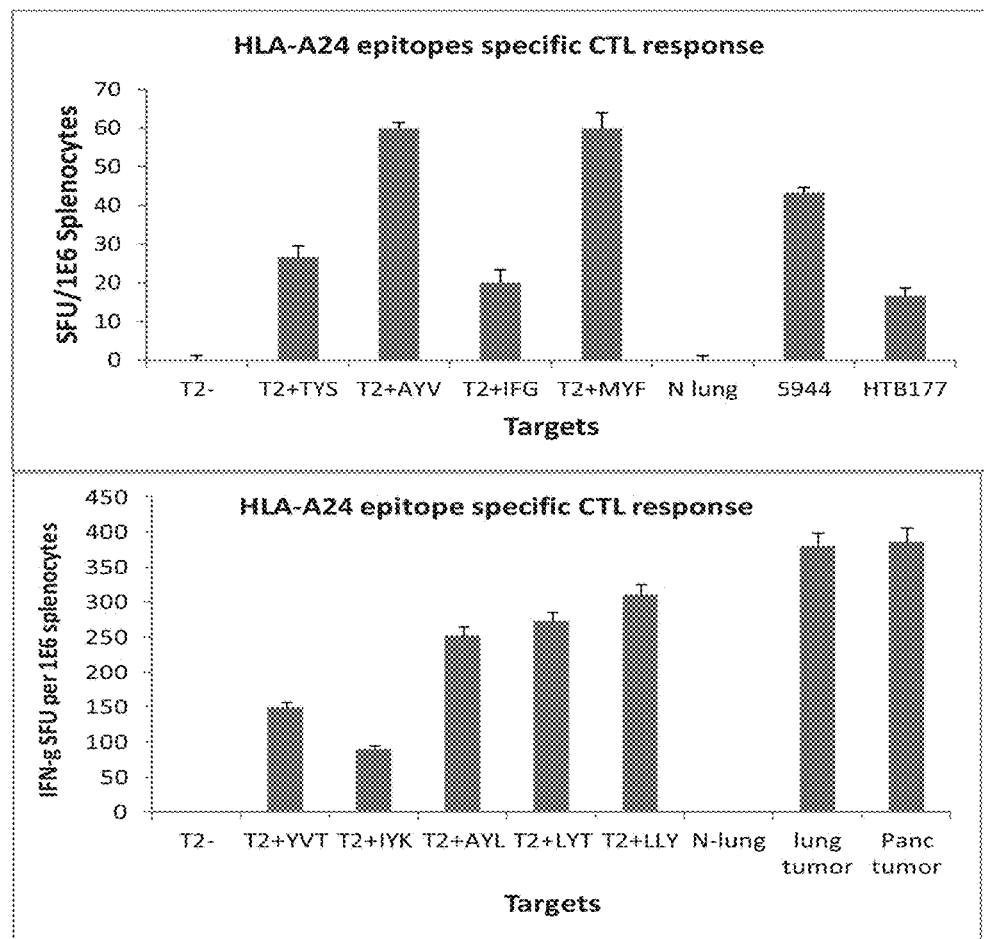

CYTOTOXIC T LYMPHOCYTE INDUCING IMMUNOGENS FOR PREVENTION TREATMENT AND DIAGNOSIS OF CANCER

CROSS REFERENCE TO RELATED APPLICATIONS

This application is a divisional application of U.S. application Ser. No. 14/344,048, filed Mar. 10, 2014, which is the US national application of PCT/US2012/054826, filed on 12 Sep. 2012, which claims priority to U.S. Provisional Application No. 61/533,852, filed on 13 Sep. 2011, now expired, and 61/611,725, filed 16 Mar. 2012, now expired, the disclosures of which are herein incorporated by reference in its entirety.

This invention was made with Government support under Grant Number W81XWH-08-1-0225 awarded by the Department of Defense (ARMY/MRMC). The Government has certain rights in the invention.

FIELD OF THE INVENTION

The present invention relates generally to the field of immunogens whose structures incorporate polypeptides comprising epitopic peptides derived from proteins expressed by cancer cells and to uses of said immunogens in eliciting cytotoxic T lymphocyte (CTL) responses for the diagnosis, prevention and treatment of cancer, preferably carcinoma, most preferably ovarian carcinoma.

BACKGROUND OF THE INVENTION

The mammalian immune system has evolved a variety of mechanisms to protect the host from cancerous cells, an important component of this response being mediated by cells referred to as T cells. Cytotoxic T lymphocytes (CTLs) are specialized T cells that function primarily by recognizing and killing cancerous cells or infected cells, but also by secreting soluble molecules referred to as cytokines that can mediate a variety of effects on the immune system.

Evidence suggests that immunotherapy designed to stimulate a tumor-specific CTL response would be effective in controlling cancer. For example, it has been shown that human CTLs recognize sarcomas (Slovin, S. F. et al., J. Immunol., 137:3042-3048, (1987)), renal cell carcinomas (Schendel, D. J. et al., J. Immunol., 151:4209-4220, (1993)), colorectal carcinomas (Jacob, L. et al., Int. J. Cancer, 71:325-332, (1997)), ovarian carcinomas (Ioannides, C. G. et al., J. Immunol., 146:1700-1707, (1991)) (Peoples, G. E. et al., Surgery, 114:227-234, (1993)), pancreatic carcinomas (Peiper, M. et al., Eur. J. Immunol., 27:1115-1123, (1997); Wolfel, T. et al., Int. J. Cancer, 54:636-644, (1993)), squamous tumors of the head and neck (Yasumura, S. et al., Cancer Res., 53:1461-1468, (1993)), and squamous carcinomas of the lung (Slingluff, C. L. Jr et al., Cancer Res., 54:2731-2737, (1994); Yoshino, I. et al., Cancer Res., 54:3387-3390, (1994)). The largest number of reports of human tumor-reactive CTLs have concerned cancers (Boon, T. et al., Ann. Rev. Immunol., 12:337-365, (1994)). The ability of tumor-specific CTLs to mediate tumor regression, in both human (Rosenberg, S. A. et al., N. Engl. J. Med., 319:1676-1680, (1988)) and animal models (Celluzzi, C. M. et al., J. Exp. Med., 183:283-287, (1996); Mayordomo, J. I. et al., Nat. Med., 1:1297-1302, (1995); Zitvogel, L. et al., J. Exp. Med., 183:87-97, (1996)), suggests that methods directed at increasing CTL activity would likely have a beneficial effect with respect to tumor treatment.

In order for CTLs to kill or secrete cytokines in response to a cancer cell, the CTL must first recognize that cell as being cancerous. This process involves the interaction of the T cell receptor, located on the surface of the CTL, with what is generically referred to as an MHC-peptide complex which is located on the surface of the cancerous cell. MHC (Major Histocompatibility Complex)-encoded molecules have been subdivided into two types, and are referred to as class I and class II MHC-encoded molecules.

In the human immune system, MHC molecules are referred to as human 30 leukocyte antigens (ILA). Within the MHC, located on chromosome six, are three different genetic loci that encode for class I MHC molecules. MHC molecules encoded at these loci are referred to as HLA-A, HLA-B, and HLA-C. The genes that can be encoded at each of these loci are extremely polymorphic, and thus, different individuals within the population express different class I MHC molecules on the surface of their cells. HLA-A1, HLA-A2, HLA-A24, HLA-A3, HLA-B7, and HLA-B8 are examples of different class I MHC molecules that can be expressed from these loci. The present disclosure involves peptides that are associated with the HLA-A1, HLAA2, or HLA-A24 molecules, HLA-A1 supertypes, HLA-A2 supertypes, and HLA-A24 supertypes. A supertype is a group of HLA molecules that present at least one shared epitope. The present disclosure involves peptides that are associated with HLA molecules, and with the genes and proteins from which these peptides are derived.

The peptides that associate with the MHC molecules can either be derived from proteins made within the cell, in which case they typically associate with class I MHC molecules (Rock, K. L. and Golde, U., Ann. Rev. Immunol., 17:739-779, (1999)) or they can be derived from proteins that are acquired from outside of the cell, in which case they typically associate with class II MHC molecules (Watts, C., Ann. Rev. Immunol., 15:821-850, (1997)). Peptides that evoke a cancer-specific CTL response most typically associate with class I MHC molecules. The peptides that associate with a class I MHC molecule are typically nine amino acids in length, but can vary from a minimum length of eight amino acids to a maximum of fourteen amino acids in length. A class I MHC molecule with its bound peptide, or a class II MHC molecule with its bound peptide, is referred to as an MHC-peptide complex.

Once bound to the class I MHC molecule and displayed on the surface of a cell, the peptides are recognized by antigen-specific receptors on CTLs. Mere expression of the class I MHC molecule itself is insufficient to trigger the CTL to kill the target cell if the antigenic peptide is not bound to the class I MHC molecule. Several methods have been developed to identify the peptides recognized by CTL, each method relying on the ability of a CTL to recognize and kill only those cells expressing the appropriate class I MHC molecule with the peptide bound to it (Rosenberg, S. A., Immunity, 10:281-287, (1999)). Such peptides can be derived from a non-self source, such as a pathogen (for example, following the infection of a cell by a bacterium or a virus) or from a self-derived protein within a cell, such as a cancerous cell. Examples of sources of self-derived proteins in cancerous cells have been reviewed (Gilboa, E., Immunity, 11:263-270, (1999); Rosenberg, S. A., Immunity, 10:281-287, (1999)) and include: (i) mutated genes; (ii) aberrantly expressed genes such as an alternative open reading frame or through an intron-exon boundary; (iii) normal genes that are selectively expressed in only the tumor and the testis; and (iv) normal differentiation genes that are expressed in the tumor and the normal cellular counterpart.

Four different methodologies have typically been used for identifying the peptides that are recognized by CTLs. These are: (i) the genetic method; (2) motif analysis; (3) SErological analysis of REcombinant cDNA expression libraries (SEREX™); and (iv) the immunological and analytical chemistry combined approach or the direct identification of epitopes isolated from MHC molecules on the target cells.

Direct identification method involves a combination of cellular immunology and mass spectrometry. This approach involves the actual identification of endogenous CTL epitopes present on the cell surface by sequencing the naturally occurring peptides associated with class I MHC molecules. In this approach, cells are first lysed in a detergent solution, the peptides associated with the class I MHC molecules are purified, and the peptides are fractionated by high performance liquid chromatography (HPLC). Peptide sequencing is readily performed by tandem mass spectrometry (Henderson, R. A. et al., Proc. Natl. Acad. Sci. U.S.A, 90:10275-1062, (1993); Hogan, K. T. et al., Cancer Res., 58:5144-5150, (1998); Hunt, D. F. et al., Science, 255:1261-1263, (1992); Slingluff, C. L. Jr et al., J. Immunol., 150: 2955-2963, (1993)).

Immunization with cancer-derived, class I MHC molecule-associated peptides, or with a parent, or original protein or precursor polypeptide that contains the peptide, or with a gene that encodes a polypeptide or protein containing the peptide, are forms of immunotherapy that can be employed in the treatment of cancer. These forms of immunotherapy require that immunogens be identified so that they can be formulated into an appropriate vaccine. Although a variety of cancer-derived antigens have been identified (Rosenberg, S. A., Immunity, 10:281-287, (1999)), not all of these are appropriate for broad-based immunotherapy because the expression of some peptides is limited to the tumor derived from a specific patient. Furthermore, the number of class I MHC molecules from which tumor-derived peptides have been discovered is largely restricted to HLA-A2. Thus, it would be useful to identify peptides that complex with class I MHC molecules other than HLA-A2. Such peptides would be particularly useful in the treatment of cancer patients who do not express the HLA-A2 molecule for example HLA-A24 supertypes, HLA-A1 supertypes, HLA-A2 supertypes and HLA-A3 supertypes. Identification of and immunization with a cancer-derived parent or original protein or with a gene that encodes the parent protein is significant because the protein can be administered to patients of any HLA type, because proteins that pass through the MHC pathway are processed in vivo to the correct patients own HLA type-specific epitopes.

It is also particularly useful to identify antigenic peptides that are derived from different parent proteins, even if the derived peptides associate with the same class I MHC molecule. Because an active immune response can result in the outgrowth of tumor cells that have lost the expression of a particular precursor protein for a given antigenic peptide, it is advantageous to stimulate an immune response against peptides derived from more than one protein, as the chances of the tumor cell losing the expression of two or more proteins is the multiple of the chances of losing each of the individual proteins.

In addition, it is also useful to identify MHC class I epitopes presented by tumor cells exposed to chemotherapeutic agents or other treatments such as radiation, heat or other physical methods, for potential immunotherapy treatments following or combined with these first line interventions of cancers. Treatment such as chemotherapy and radiation can modulate the cell surface antigens in tumor cells which could either increase the susceptibility of tumor cells for T cell or antibody recognition or modify the tumor microenvironment to favor the recruitment and expansion of tumor specific cytotoxic T cells Other investigators have also reported substantial progress in enhancing the clinical effectiveness of cancer vaccines by using them in combination with other therapeutic modalities. Clinical studies in pancreatic and lung cancer have demonstrated that patients treated with vaccines that elicit an immune response will stimulate enhanced responses to subsequent treatments, including time of progression-free survival and overall survival (Antonia, Mirza et al. 2006; Petrylak 2006; Schlom, Arlen et al. 2007). Preclinical studies in renal, colon, pancreatic, head and neck and esophageal cancers also suggest that drugs such as cisplatin and gemcitabine (Gelbard, Garnett et al. 2006) and 5-fluorouracil (Aquino, Prete et al. 2000) induce alterations in tumor phenotype that increase tumor susceptibility to T cell lysis. Drug and radiation therapy have been used in combination with vaccine therapy to augment vaccine-induced T cell tumor killing in vivo (Schlom, Arlen et al. 2007). In other studies, initial vaccine treatment was shown to augment the efficacy of subsequent radiation therapy (Arlen, Gulley et al. 2005; Gribben, Ryan et al. 2005; Antonia, Mirza et al. 2006; Arlen, Gulley et al. 2006; Petrylak 2006; Madan 2007), all of which strongly suggest that efficacy and specificity can be significantly enhanced by the use of combinations that use different modalities to effect tumor killing. The induction of CTL against resistance genes in other tumor types has also been reported (Meier, Reker et al. 2005).

Treatment with chemotherapeutic agents has been shown to alter MHC class I associated peptide repertoire, which could generate novel antigenic epitopes presented on tumor cell surface. Identifying these antigenic epitopes will greatly facilitate the generation of chemotherapy-stimulated peptide vaccines for the induction of protective immune response and create a rationale for optimal cancer vaccine therapy in combination with chemotherapy. Chemotherapy treatment would generate a specific pool of antigens processed through the MHC class I pathway in cancer cells. Therapeutic vaccine based on these neo antigens would induce cancer specific CTL responses that would augment the local effects of the chemotherapy and potentially make the cancer cells more susceptible for CTL killing to eradicate microscopic metastatic disease.

SUMMARY OF THE INVENTION

The present invention relates to Immunogens comprising polypeptides with amino acid sequences comprising epitopic sequences selected from the sequences of SEQ ID NO: 1-53 and which immunogens facilitate a cytotoxic T lymphocyte (CTL)-mediated immune response against various cancers. The present invention also relates to nucleic acid molecules that encode for the polypeptides and/or the full length proteins, their isoforms and splice variants from which the polypeptides are derived, of such immunogens, and which can also be used to facilitate an immune response against cancer.

The present invention provides compositions comprising the immunogen described herein, and polynucleotides that direct the synthesis of such polypeptides, whereby the oligopeptides and polypeptides of such immunogens are capable of inducing a CTL response against cells expressing a protein comprising an epitopic sequence of at least one of SEQ ID NO: 1-53. The cells are usually cancer cells treated or untreated with chemotherapy, preferably carcinoma cells, most preferably ovarian, breast, pancreatic, lung and colon carcinomas expressing such proteins.

The present invention further relates to polynucleotides comprising the gene coding for a polypeptide of the immunogens disclosed herein. The methods may involve contacting the CTL with the immunogenic peptide in vivo, in which case the peptides, polypeptides, and polynucleotides of the invention are used as vaccines, and will be delivered as a pharmaceutical composition comprising a pharmaceutically acceptable carrier or delivery system and the immunogen, typically along with an adjuvant or one or more cytokines.

Alternatively, the immunogens of the present invention can be used to induce a CTL response in vitro. The generated CTL can then be introduced into a patient with cancer, more specifically ovarian carcinoma, pancreatic carcinoma, colorectal carcinoma, lung carcinoma, or breast carcinoma. Alternatively, the ability to generate CTL in vitro could serve as a diagnostic for cancer generally, including ovarian carcinoma, pancreatic carcinoma, colorectal carcinoma, lung carcinoma, or breast carcinoma.

BRIEF DESCRIPTION OF THE DRAWINGS

FIG. 2: In vivo characterization of cancer epitopes. Panel A: HLA-A2 transgenic mouse model data—Lung, Colon, Pancreatic cancer targets. Panel B: HLA-A24 transgenic mouse model data—Lung, Pancreatic cancer targets.

DETAILED DESCRIPTION OF THE INVENTION

Figure 1:
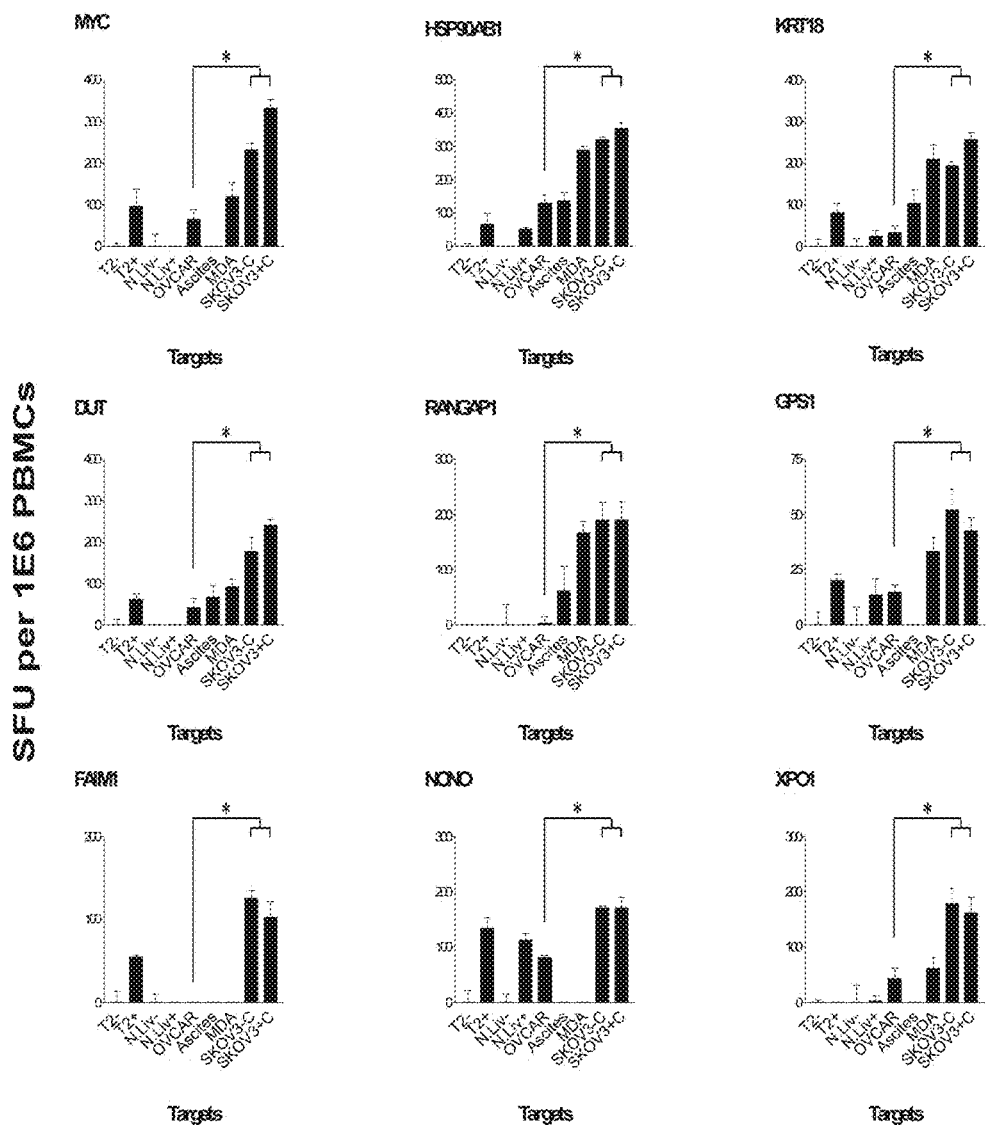
FIG. 1: In vitro characterization of cancer epitopes

As used herein and except as noted otherwise, all terms are defined as follows. The term "peptide" is used herein to designate a series of amino acid residues, connected one to the other typically by peptide bonds between the alpha-amino and carbonyl groups of the adjacent amino acids. The peptides are typically 9 amino acids in length, but can be as short as 8 amino acids in length, and as long as 14 amino acids in length.

The term "oligopeptide" is used herein to designate a series of amino acid residues, connected one to the other typically by peptide bonds between the alpha-amino and carbonyl groups of the adjacent amino acids. The length of the oligopeptide is not critical to the invention as long as the correct epitope or epitopes are maintained therein. The oligopeptides are typically 30 to about 40 amino acid residues in length, and greater than about 14 amino acids in length.

The term "polypeptide" designates a series of amino acid residues, connected one to the other typically by peptide bonds between the alpha-amino and carbonyl groups of the adjacent amino acids. In contrast to the terms peptide or oligopeptide, the term polypeptide is meant to refer to protein molecules of longer than about 40 residues in length.

A peptide, oligopeptide, polypeptide, protein, or polynucleotide coding for such a molecule is "immunogenic" (and thus an "immunogen" within the present invention) if it is capable of inducing an immune response. In the case of the present invention, immunogenicity is more specifically defined as the ability to induce a CTL-mediated response. Thus, an "immunogen" would be a molecule that is capable of inducing an immune response, and in the case of the present invention, a molecule capable of inducing a CTL response. A T cell "epitope" is a short peptide molecule that binds to a class I or II MHC molecule and that is subsequently recognized by a T cell. T cell epitopes that bind to class I MHC molecules are typically 8-14 amino acids in length, and most typically 9 amino acids in length.

Three different genetic loci encode for class I MHC molecules: HLA-A, HLA-B, and HLA-C. HLA-A1, HLA-A2, HLA-A24 and HLA-A3 are examples of different class I MHC molecules that can be expressed from these loci. The present invention also involves peptides that are associated with HLA-A2 supertypes, HLA-A24 supertypes, and HLA-A3 supertypes. A supertype is a group of HLA molecules that present at least one shared epitope. MHC molecule peptides that have been found to bind to one member of the MHC allele supertype family (A1 for example) are thought to be likely to bind to other members of the same supertype family (A32 for example).

As used herein, reference to a DNA sequence includes both single stranded and double stranded DNA. The term "coding region" refers to that portion of a gene that either naturally or normally codes for the expression product of that gene in its natural genomic environment, i.e., the region coding in vivo for the native expression product of the gene. The coding region can be from a normal, mutated or altered gene, or can even be from a DNA sequence, or gene, wholly synthesized in the laboratory using methods well known to those of skill in the art of DNA synthesis.

The term "nucleotide sequence" refers to a heteropolymer of deoxyribonucleotides. The nucleotide sequence encoding for a particular peptide, oligopeptide, or polypeptide may be naturally occurring or they may be synthetically constructed.

The term "expression product" means that polypeptide or protein that is the natural translation product of the gene and any nucleic acid sequence coding equivalents resulting from genetic code degeneracy and thus coding for the same amino acid(s).

The term "fragment," when referring to a coding sequence, means a portion of DNA comprising less than the complete coding region whose expression product retains essentially the same biological or immunological function or activity as the expression product of the complete coding region.

The term "DNA segment" refers to a DNA polymer, in the form of a separate fragment or as a component of a larger DNA construct, that has been derived from DNA isolated at least once in substantially pure form, i.e., free of contaminating endogenous materials and in a quantity or concentration enabling identification, manipulation, and recovery of the segment and its component nucleotide sequences by standard biochemical methods. The term "primer" means a short nucleic acid sequence that is paired with one strand of DNA and provides a free 3'OH end at which a DNA polymerase starts synthesis of a deoxyribonucleotide chain.

The term "promoter" means a region of DNA involved in binding of RNA polymerase to initiate transcription.

The term "open reading frame (ORF)" means a series of triplets coding for amino acids without any termination codons and is a sequence (potentially) translatable into protein.

The term "isolated" means that the material is removed from its original environment (e.g., the natural environment if it is naturally occurring).

The polynucleotides, and recombinant or immunogenic polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art.

The nucleic acids and polypeptide expression products disclosed according to the present invention, as well as expression vectors containing such nucleic acids and/or such polypeptides, may be in "enriched form." As used herein, the term "enriched" means that the concentration of the material is at least about 2, 5, 10, 100, or 1000 times its natural concentration.

The term "active fragment" means a fragment that generates an immune response (i.e., has immunogenic activity) when administered, alone or optionally with a suitable adjuvant, to an animal, such as a mammal, for example, a human, and also including a rabbit or a mouse, such immune response taking the form of stimulating a CTL response within the recipient, such as a human. Alternatively, the "active fragment" may also be used to induce a CTL response in vitro.

As used herein, the terms "portion," "segment," and "fragment," when used in relation to polypeptides, refer to a continuous sequence of residues, such as amino acid residues, which sequence forms a subset of a larger sequence. This means that any such fragment will necessarily contain as part of its amino acid sequence a segment, fragment or portion, that is substantially identical, if not exactly identical to the naturally occurring original or "parent" proteins of the peptides of SEQ ID NO: 1-53.

In accordance with the present invention, the term "percent identity" or "percent identical," when referring to a sequence, means that a sequence is compared to a claimed or described sequence after alignment of the sequence to be compared (the "Compared Sequence") with the described or claimed sequence (the "Reference Sequence").

The present invention relates generally to immunogens and immunogenic compositions, and methods of use thereof, for the prevention, treatment, and diagnosis of cancer, especially carcinomas, including lung, colon, breast, pancreatic and ovarian carcinomas. Disclosed according to the invention are immunogens comprising proteins or polypeptides whose amino acid sequences comprises one or more epitopic oligopeptides with sequences selected from the group SEQ ID NO: 1-53. In addition, the invention further relates to polynucleotides that can be used to stimulate a CTL response against various cancers, including ovarian, breast, pancreatic, colon, and lung carcinoma.

In accordance with the present invention there are disclosed specific oligopeptide sequences with amino acid sequences shown in SEQ ID NO: 1-53 which represent epitopic peptides (i.e. immunogenic oligopeptide sequences) of at least about 8 amino acids in length, preferably about 9 amino acids in length (i.e., nonapeptides), and no longer than about 14 amino acids in length and present as part of a larger structure, such as a polypeptide or full length protein.

While the use of specific peptides is restricted to use in patients having certain HLA types or HLA supertypes, there is no such restriction on the use of the parent protein as an immunogen. When the parent protein or immunogen is presented to the antigen processing pathway, it will be appropriately fragmented, processed and presented in the context of HLA type(s) present in the patient.

The polypeptides forming the immunogens of the present invention have amino acid sequences that comprise at least one stretch, possibly two, three, four, or more stretches of about 8 to 10 or up to 14 residues in length and which stretches differ in amino acid sequence from the sequences of SEQ ID NO: 1-53 by no more than about 1 amino acid residue, preferably a conservative amino acid residue, especially amino acids of the same general chemical character, such as where they are hydrophobic amino acids.

Said polypeptides can be of any desired length so long as they have immunogenic activity in that they are able, under a given set of desirable conditions, to elicit in vitro or in vivo the activation of cytotoxic T lymphocytes (CTLs) (i.e., a CTL response) against a presentation of a cancer specific protein, especially a carcinoma or sarcoma specific protein where said proteins are presented in vitro or in vivo by an antigen presenting cell (APC). The proteins and polypeptides forming the immunogens of the present invention can be naturally occurring or may be synthesized chemically.

The present invention is also directed to an isolated polypeptide, especially one having immunogenic activity, the sequence of which comprises within it one or more stretches comprising any 2 or more of the sequences of SEQ ID NO: 1-53 and in any relative quantities and wherein said sequences may differ by one amino acid residues from the sequences of SEQ ID NO: 1-53 in any given stretch of 8 to 10, or up to 14 amino acid residues. Thus, within the present invention, by way of a non-limiting example only, such polypeptide may contain as part of its amino acid sequence, nanopeptide fragments having up to 8 amino acids identical to a sequence of SEQ ID NO: 1, 2, 7, 8 such that the polypeptide comprises, in a specific embodiment, 2 segments with at least 8 residues identical to SEQ ID NO: 1 and SEQ ID NO: 2 and one segment with at least 8 residues identical to SEQ ID NO: 7. In other embodiments, other combinations and permutations of the epitopic sequences disclosed herein may be part of an immunogen of the present invention or of such a polypeptide so long as any such polypeptide comprises at least 2 such epitopes, whether such epitopes are different or the same. Thus, in a specific embodiment, a polypeptide of the present invention may comprise 2 copies of the sequence of SEQ ID NO: 2 at some point or points within its length. Of course, any combinations and permutations of the epitopes disclosed herein, as long as they are present at least two in number in such polypeptides, are expressly contemplated.

All of the epitopic peptides of SEQ ID NO: 1-53 are derived from proteins expressed by cancer cells and sequences and were identified through the method of High Through-put Sequencing (HTPS).

Oligopeptides as disclosed herein may themselves be prepared by methods well known to those skilled in the art. (Grant, G. A., Synthetic Peptides: A User's Guide, 1992, W. H. Freeman and Company, New York; Coligan, J. E. et al, Current Protocols in Protein Science, 1999, John Wiley & Sons, Inc., New York).

Besides the sequences of SEQ ID NO:1-53, the proteins and polypeptides forming the immunogens of the present invention may also comprise one or more other immunogenic amino acid stretches known to be associated with cancer, and more specifically with carcinomas including pancreatic carcinoma, colorectal carcinoma, lung carcinoma, or breast carcinoma, and which may stimulate a CTL response whereby the immunogenic peptides associate with HLA-A2, HLA-A24, HLA-A1 or A3, HLA supertypes, or any class I MHC (i.e., MHC-1) molecule.

The immunogens of the present invention can be in the form of a composition of one or more of the different immunogens and wherein each immunogen is present in any desired relative abundance. Such compositions can be homogeneous or heterogeneous with respect to the individual immunogenic peptide components present therein, having only one or more than one of such peptides.

The oligopeptides and polypeptides useful in practicing the present invention may be derived by fractionation of naturally occurring proteins by methods such as protease treatment, or they may be produced by recombinant or synthetic methodologies that are well known and clear to the skilled artisan (Ausubel, F. M. et al, Current Protocols in Molecular Biology, 1999, John Wiley & Sons, Inc., New York; Coligan, J. B. et al, Current Protocols in Protein Science, 1999, John Wiley & Sons, Inc., New York; Molecular Cloning: A Laboratory Manual, 1989, Cold Spring Harbor Laboratory Press, Cold Spring Harbor). The polypeptide may comprise a recombinant or synthetic polypeptide that comprises at least one of SEQ ID NO:1-53 which sequences may also be present in multiple copies. Thus, oligopeptides and polypeptides of the present invention may have one, two, three, or more such immunogenic peptides within the amino acid sequence of said oligopeptides and polypeptides, and said immunogenic peptides, or epitopes, may be the same or may be different, or may have any number of such sequences wherein some of them are identical to each other in amino acid sequence while others within the same polypeptide sequence are different from each other and said epitopic sequences may occur in any order within said immunogenic polypeptide sequence. The location of such sequences within the sequence of a polypeptide forming an immunogen of the invention may affect relative immunogenic activity. In addition, immunogens of the present invention may comprise more than one protein comprising the amino acid sequences disclosed herein. Such polypeptides may be part of a single composition or may themselves be covalently or non-covalently linked to each other.

The immunogenic peptides disclosed herein may also be linked directly to, or through a spacer or linker to: an immunogenic carrier such as serum albumin, tetanus toxoid, keyhole limpet hemocyanin, dextran, or a recombinant virus particle; an immunogenic peptide known to stimulate a T helper cell type immune response; a cytokine such as interferon gamma or GMCSF; a targeting agent such as an antibody or receptor ligand; a stabilizing agent such as a lipid; or a conjugate of a plurality of epitopes to a branched lysine core structure, such as the so-called "multiple antigenic peptide" described in (Posneft, D. N. et al., J. Biol. Chem., 263:1719-1725, (1988)); a compound such as polyethylene glycol to increase the half life of the peptide; or additional amino acids such as a leader or secretory sequence, or a sequence employed for the purification of the mature sequence. Spacers and linkers typically comprise relatively small, neutral molecules, such as amino acids and which are substantially uncharged under physiological conditions. Such spacers are typically selected from the group of nonpolar or neutral polar amino acids, such as glycine, alanine, serine and other similar amino acids. Such optional spacers or linkers need not comprise the same residues and thus may be either homo- or hetero-oligomers. When present, such linkers will commonly be of length at least one or two, commonly 3, 4, 5, 6, and possibly as much as 10 or even up to 20 residues (in the case of amino acids). In addition, such linkers need not be composed of amino acids but any oligomeric structures will do as well so long as they provide the correct spacing so as to optimize the desired level of immunogenic activity of the immunogens of the present invention. The immunogen may therefore take any form that is capable of eliciting a CTL response.

In addition, the immunogenic peptides of the present invention may be part of an immunogenic structure via attachments other than conventional peptide bonds. Thus, any manner of attaching the peptides of the invention to an immunogen of the invention, such as an immunogenic polypeptide as disclosed herein, could provide an immunogenic structure as claimed herein. Thus, immunogens, such as proteins, oligopeptides and polypeptides of the invention, are structures that contain the peptides disclosed according to the present invention but such immunogenic peptides may not necessarily be attached thereto by the conventional means of using ordinary peptide bounds. The immunogens of the present invention simply contain such peptides as part of their makeup, but how such peptides are to be combined to form the final immunogen is left to the talent and imagination of the user and is in no way restricted or limited by the disclosure contained herein.

The peptides that are naturally processed and bound to a class I MHC molecule, and which are recognized by a tumor-specific CTL, need not be the optimal peptides for stimulating a CTL response. See, for example, (Parkhurst, M. R. et al., J. Immunol., 157:2539-2548, (1996); Rosenberg, S. A. et al., Nat. Med., 4:321-327, (1998)). Thus, there can be utility in modifying a peptide, such that it more readily induces a CTL response. Generally, peptides may be modified at two types of positions. The peptides may be modified at amino acid residues that are predicted to interact with the class I MHC molecule, in which case the goal is to create a peptide that has a higher affinity for the class I MHC molecule than does the original peptide. The peptides can also be modified at amino acid residues that are predicted to interact with the T cell receptor on the CTL, in which case the goal is to create a peptide that has a higher affinity for the T cell receptor than does the original peptide. Both of these types of modifications can result in a variant peptide that is related to an original peptide, but which is better able to induce a CTL response than is the original peptide. As used herein, the term "original peptide" means an oligopeptide with the amino acid sequence selected from SEQ ID NO: 1-53.

The original peptides disclosed herein can be modified by the substitution of one or more residues at different, possibly selective, sites within the peptide chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1—small aliphatic, nonpolar or slightly polar residues (Ala, Ser, Thr, Pro, Gly); Group 2—polar, negatively charged residues and their amides (Asp, Asn, Glu, Gln); Group 3—polar, positively charged residues (His, Arg, Lys); Group 4—large, aliphatic, nonpolar residues (Met, Leu, lie, Val, Cys); and Group 4—large, aromatic residues (Phe, Tyr, Trp).

Less conservative substitutions might involve the replacement of one amino acid by another that has similar characteristics but is somewhat different in size, such as replacement of an alanine by an isoleucine residue. Highly nonconservative replacements might involve substituting an acidic amino acid for one that is polar, or even for one that is basic in character. Such radical substitutions cannot, however, be dismissed as potentially ineffective since chemical effects are not totally predictable and radical substitutions might well give rise to serendipitous effects not otherwise predictable from simple chemical principles.

Of course, such substitutions may involve structures other than the common L-amino acids. Thus, D-amino acids might be substituted for the L-amino acids commonly found in the antigenic peptides of the invention and yet still be encompassed by the disclosure herein. In addition, amino acids possessing non-standard R groups (i.e., R groups other than those found in the common 20 amino acids of natural proteins) may also be used for substitution purposes to produce immunogens and immunogenic polypeptides according to the present invention.

If substitutions at more than one position are found to result in a peptide with substantially equivalent or greater antigenic activity as defined below, then combinations of those substitutions will be tested to determine if the combined substitutions result in additive or syngeneic effects on the antigenicity of the peptide. At most, no more than 4 positions within the peptide would simultaneously be substituted.

Thus, the epitopes of the present invention may be identical to naturally occurring tumor-associated or tumor-specific epitopes or may include epitopes that differ by no more than 4 residues from the reference peptide, as long as they have substantially identical antigenic activity.

It should be appreciated that an immunogen may consist only of a peptide of SEQ ID NO:1-53, or comprise a peptide of SEQ ID NO:1-53, or comprise a plurality of peptides selected from SEQ ID NO: 1-53, or comprise a polypeptide that itself comprises one or more of the epitopic peptides of SEQ ID NO: 1-53.

The immunogenic peptides and polypeptides of the invention can be prepared synthetically, by recombinant DNA technology, or they can be isolated from natural sources such as tumor cells expressing the original protein product.

The polypeptides and oligopeptides disclosed herein can be synthesized in solution or on a solid support in accordance with conventional techniques.

Recombinant DNA technology may be employed wherein a nucleotide sequence that encodes an immunogenic peptide or polypeptide of interest is inserted into an expression vector, transformed or transfected into an appropriate host cell, and cultivated under conditions suitable for expression. These procedures are well known in the art to the skilled artisan, as described in (Coligan, J. E. et al, Current Protocols in Immunology, 1999, John Wiley & Sons, Inc., New York; Ausubel, F. M. et al, Current Protocols in Molecular Biology, 1999, John Wiley & Sons, Inc., New York; Molecular Cloning: A Laboratory Manual, 1989, Cold Spring Harbor Laboratory Press, Cold Spring Harbor). Thus, recombinantly produced peptides or polypeptides can be used as the immunogens of the invention.

The coding sequences for peptides of the length contemplated herein can be synthesized on commercially available automated DNA synthesizers using protocols that are well known in the art. See for example, (Grant, G. A., Synthetic Peptides: A User's Guide, 1992, W. H. Freeman and Company, New York; Coligan, J. E. et al, Current Protocols in Protein Science, 1999, John Wiley & Sons, Inc., New York). The coding sequences can also be modified such that a peptide or polypeptide will be produced that incorporates a desired amino acid substitution. The coding sequence can be provided with appropriate linkers, be ligated into suitable expression vectors that are commonly available in the art, and the resulting DNA or RNA molecule can be transformed or transfected into suitable hosts to produce the desired fusion protein. A number of such vectors and suitable host systems are available, and their selection is left to the skilled artisan. For expression of the fusion proteins, the coding sequence will be provided with operably linked start and stop codons, promoter and terminator regions, and a replication system to provide an expression vector for expression in the desired host cell. Host cells are genetically engineered (transduced or transformed or transfected) with the vectors of this invention which may be, for example, a cloning vector or an expression vector. The vector may be, for example, in the form of a plasmid, a viral particle, a phage, etc. and the culture conditions for expression, and will be apparent to the ordinarily skilled artisan.

More particularly, the present invention also includes recombinant constructs comprising one or more of the sequences as broadly described above. Large numbers of suitable vectors and promoters are known to those of skill in the art, and are commercially available.

In a further embodiment, the present invention relates to host cells containing the above-described constructs. The host cell can be a higher eukaryotic cell, such as any mammalian cell capable of expressing a compatible vector, or a lower eukaryotic cell, such as a yeast cell, or the host cell can be a prokaryotic cell, such as a bacterial cell. Such cells can routinely be utilized for assaying CTL activity by having said genetically engineered, or recombinant, host cells express the immunogenic peptides of the present invention.

The polypeptide can be recovered and purified from recombinant cell cultures by methods known to those of skill in the art including not limited to ammonium sulfate or ethanol precipitation, acid extraction, anion or cation exchange chromatography, affinity chromatography, and lectin chromatography. Protein refolding steps can be used, as necessary, in completing configuration of the mature protein. The immunogenic peptides of the present invention may be used to elicit CTLs ex vivo from either healthy individuals or from cancer patients, such as breast carcinoma, colorectal carcinoma, lung carcinoma, ovarian carcinoma, or pancreatic carcinoma. Such responses are induced by incubating in tissue culture the individual's CTL precursor lymphocytes together with a source of antigen presenting cells and the appropriate immunogenic peptide. (Ljunggren, H.-G. et al., Nature, 346:476-480, (1990)) (Zeh, H. J., III et al., Hum. Immunol., 39:79-86, (1994)) Oligopeptides and polypeptides that comprise one or more of the peptides of the invention can be provided to antigen presenting cells in culture to generate CTL ex vivo. Many in vitro CTL stimulation protocols have been described and the choice of which one to use is well within the knowledge of the skilled artisan. The peptide-specific CTL can be further expanded to large numbers by treatment with anti-CD3 antibody. For example, see (Riddell, S. R. and Greenberg, P. D., J. Immunol. Methods, 128:189-201, (1990); Walter, E. A. et al., N. Engl. J. Med., 333:1038-1044, (1995)).

Antigen presenting cells suitable for stimulating an in vitro CTL response that is specific for one or more of the peptides of the invention can also be prepared by introducing polynucleotide vectors encoding the sequences into the cells. A variety of approaches are known in the art that allow polynucleotides to be introduced and expressed in a cell, thus providing one or more peptides of the invention to the class I MHC molecule binding pathway.

By preparing the stimulator cells used to generate an in vitro CTL response in different ways, it is possible to control the peptide specificity of CTL response. More broadly, stimulator cells, and more specifically dendritic cells, can be incubated in the presence of the whole parent protein. As a further alternative, stimulator cells, and more specifically dendritic cells, can be transduced or transfected with RNA or DNA comprising the polynucleotide sequence encoding the protein. Under these alternative conditions, peptide epitopes that are naturally cleaved out of the protein, and which are generated in addition to peptide epitopes of SEQ ID NO: 1-53 can associate with an appropriate class I MHC molecule, which may or may not include HLA-A1, -A2, -A24, -A3. The selection of antigen presenting cells and the type of antigen with which to stimulate the CTL, is left to the ordinary skilled artisan.

In certain embodiments, the methods of the present invention include a method for inducing a CTL response in vitro that is specific for a tumor cell expressing a molecule from A1, A2, A24 or A3 supertypes, whereby the method comprises contacting a CTL precursor lymphocyte with an antigen presenting cell that has bound an immunogen comprising one or more of the peptides disclosed according to the invention.

In specific embodiments, the methods of the present invention include a method for inducing a CTL response in vitro that is specific for a tumor cell expressing a molecule from A1, A2, A3 or A24 supertypes, whereby the method comprises contacting a CTL precursor lymphocyte with an antigen presenting cell that has exogenously acquired an immunogenic oligopeptide or polypeptide that comprises one or more of the peptides disclosed according to the invention.

A yet additional embodiment of the present invention is directed to a process for inducing a CTL response in vitro that is specific for a tumor cell expressing a molecule from A1, A2, A24 or A3 supertypes, comprising contacting a CTL precursor lymphocyte with an antigen presenting cell that is expressing a polynucleotide coding for a polypeptide of the invention and wherein said polynucleotide is operably linked to a promoter.

A variety of techniques exist for assaying the activity of CTL. These techniques include the release of cytokines, activation or degranulation marker expression, labeling of target cells with radionuclides such as $Na_2^{51}CrO_4$ or $^3H$-thymidine, and measuring the release or retention of the radionuclides from the target cells as an index of cell death. Such assays are well-known in the art and their selection is left to the skilled artisan.

After expansion of the antigen-specific CTLs, the latter are then adoptively transferred back into the patient, where they will destroy their specific target cell. The utility of such adoptive transfer is demonstrated in North, R. J. et al. (Infect. Immun., 67:2010-2012, (1999)) and Riddell, S. R. et al. (Science, 257:238-241, (1992)). In determining the amount of cells to reinfuse, the skilled physician will be guided by the total number of cells available, the activity of the CTL as measured in vitro, and the condition of the patient. Methodology for reinfusing T cells into a patient are well known and exemplified in U.S. Pat. No. 4,844,893 to Honski, et al., and U.S. Pat. No. 4,690,915 to Rosenberg.

The peptide-specific CTL can be purified from the stimulator cells prior to infusion into the patient including not limited to antibody panning, flow cytometric sorting, and magnetic bead separation to purify the peptide-specific CTL away from any remaining non-peptide specific lymphocytes or from the stimulator cells. These methods are well known in the art, and their selection is left to the skilled artisan.

Thus, one embodiment of the present invention relates to a process for treating a subject with cancer characterized by tumor cells expressing complexes of a molecule from A1, A2, A3 or A24 supertypes, for example, HLA-A1, HLA-A2, HLA-A3 or HLA-A24, whereby CTLs produced in vitro according to the present invention are administered in an amount sufficient to destroy the tumor cells through direct lysis or to effect the destruction of the tumor cells indirectly through the elaboration of cytokines.

Another embodiment of the present invention is directed to a process for treating a subject with cancer characterized by tumor cells expressing any class I MHC molecule and an epitope of SEQ ID NO: 1-53, whereby the CTLs are produced in vitro and are specific for the epitope or original protein and are administered in an amount sufficient to destroy the tumor cells through direct lysis or to effect the destruction of the tumor cells indirectly through the elaboration of cytokines.

In the foregoing embodiments the cancer to be treated may include a breast carcinoma, a colorectal carcinoma, an ovarian carcinoma, a lung carcinoma, and pancreatic carcinoma.

The ex vivo generated CTL can be used to identify and isolate the T cell receptor molecules specific for the peptide. The genes encoding the alpha and beta chains of the T cell receptor can be cloned into an expression vector system and transferred and expressed in naive T cells from peripheral blood, T cells from lymph nodes, or T lymphocyte progenitor cells from bone marrow. These T cells, which would then be expressing a peptide-specific T cell receptor, would then have anti-tumor reactivity and could be used in adoptive therapy of cancer, and more specifically cancer, ovarian carcinoma, colorectal carcinoma, breast carcinoma, lung carcinoma, and pancreatic carcinoma.

In addition to their use for therapeutic or prophylactic purposes, the immunogenic peptides of the present invention are useful as screening and diagnostic agents. Thus, the immunogenic peptides of the present invention, together with modern techniques of gene and protein screening, make it possible to screen patients for the presence of genes encoding such peptides on cells obtained by biopsy of tumors detected in such patients. The results of such screening may help determine the efficacy of proceeding with the regimen of treatment disclosed herein using the immunogens of the present invention.

Alternatively, the immunogenic peptides disclosed herein, as well as functionally similar homologs thereof, may be used to screen a sample for the presence of CTLs that specifically recognize the corresponding epitopes. The lymphocytes to be screened in this assay will normally be obtained from the peripheral blood, but lymphocytes can be obtained from other sources, including lymph nodes, spleen, tumors, and pleural fluid. The peptides of the present invention may then be used as a diagnostic tool to evaluate the efficacy of the immunotherapeutic treatments disclosed herein. Thus, the in vitro generation of CTL as described above would be used to determine if patients are likely to respond to the peptide in vivo. Similarly, the in vitro generation of CTL could be done with samples of lymphocytes obtained from the patient before and after treatment with the peptides. Successful generation of CTL in vivo should then be recognized by a correspondingly easier ability to generate peptide-specific CTL in vitro from lymphocytes obtained following treatment in comparison to those obtained before treatment.

The oligopeptides of the invention, such as SEQ ID NO: 1-53, can also be used to prepare class I MHC/peptide tools including tetramers, pentamers or dextramers, which can be used in conjunction with flow cytometry to quantitate the frequency of peptide-specific CTL that are present in a sample of lymphocytes from an individual. Specifically, for example, class I MHC molecules comprising peptides of SEQ ID NO: 1-53, would be combined to form tetramers as exemplified in U.S. Pat. No. 5,635,363. Said MHC/peptide tools would find use in monitoring the frequency of CTLs in the peripheral blood, lymph nodes, or tumor mass of an individual undergoing immunotherapy with the peptides, proteins, or polynucleotides of the invention, and it would be expected that successful immunization would lead to an increase in the frequency of the peptide-specific CTL.

The immunogenic molecules of the invention, including vaccine compositions, may be utilized according to the present invention for purposes of preventing, suppressing or treating diseases causing the expression of the immunogenic peptides disclosed herein, such as where the antigen is being expressed by tumor cells. As used in accordance with the present invention, the term "prevention" relates to a process of prophylaxis in which an animal, especially a mammal, and most especially a human, is exposed to an immunogen of the present invention prior to the induction or onset of the disease process. This could be done where an individual has a genetic pedigree indicating a predisposition toward occurrence of the disease condition to be prevented. For example, this might be true of an individual whose ancestors show a predisposition toward certain types of cancer. Alternatively, the immunogen could be administered to the general population as is frequently done for infectious diseases. Alternatively, the term "suppression" is often used to describe a condition wherein the disease process has already begun but obvious symptoms of said condition have yet to be realized. Thus, the cells of an individual may have become cancerous but no outside signs of the disease have yet been clinically recognized. In either case, the term prophylaxis can be applied to encompass both prevention and suppression. Conversely, the term "treatment" is often utilized to mean the clinical application of agents to combat an already existing condition whose clinical presentation has already been realized in a patient. This would occur where an individual has already been diagnosed as having a tumor.

It is understood that the suitable dosage of an immunogen of the present invention will depend upon the age, sex, health, and weight of the recipient, the kind of concurrent treatment, if any, the frequency of treatment, and the nature of the effect desired. However, the most preferred dosage can be tailored to the individual subject, as determined by the researcher or clinician (i.e., successful production of a CTL-mediated response to the antigen, which response gives rise to the prevention and/or treatment desired).

For such purposes, the immunogenic compositions according to the present invention may be used against a disease condition such as cancer by administration to an individual by a variety of routes. The composition may be administered parenterally or orally, and, if parenterally, either systemically or topically. Parenteral routes include subcutaneous, intravenous, intradermal, intramuscular, intraperitoneal, intranasal, transdermal, or buccal routes. One or more such routes may be employed. Parenteral administration can be, for example, by bolus injection or by gradual perfusion over time.

Generally, vaccines are prepared as injectables, in the form of aqueous solutions or suspensions. Vaccines in an oil base are also well known such as for inhaling. Solid forms that are dissolved or suspended prior to use may also be formulated. Pharmaceutical carriers, diluents and excipients are generally added that are compatible with the active ingredients and acceptable for pharmaceutical use. Examples of such carriers include, but are not limited to, water, saline solutions, dextrose, or glycerol. Combinations of carriers may also be used. These compositions may be sterilized by conventional, well known sterilization techniques including sterile filtration. The resulting solutions may be packaged for use as is, or the aqueous solutions may be lyophilized, the lyophilized preparation being combined with sterile water before administration. Vaccine compositions may further incorporate additional substances to stabilize pH, or to function as adjuvants, wetting agents, or emulsifying agents, which can serve to improve the effectiveness of the vaccine.

The immunogens of the present invention may also be contained in any artificially created structures such as liposomes, ISCOMS, slow-releasing particles, metal and nonmetal nanoparticles and other vehicles which increase the immunogenicity and/or half-life of the peptides or polypeptides in serum. Any vehicles containing the peptides or polypeptides of the invention can be directed to the site of lymphoid cells for delivery of the selected immunogens directly to antigen presenting cells. Targeting can be achieved by incorporating additional molecules such as proteins or polysaccharides into the outer membranes of said structures, thus resulting in the delivery of the structures to particular areas of the body, or to particular cells within a given organ or tissue. Such targeting molecules may a molecule that binds to receptor on antigen presenting cells. For example antibodies or ligands that binds to CD80 or DC-SIGN receptor respectively could be used to direct any antigen delivery vehicles to dendritic cells.

The immunogens of the present invention may also be administered as solid compositions. Conventional nontoxic solid carriers including pharmaceutical grades of mannitol, lactose, starch, magnesium, cellulose, glucose, sucrose, sodium saccharin, and the like. Such solid compositions will often be administered orally, whereby a pharmaceutically acceptable nontoxic composition is formed by incorporating the peptides and polypeptides of the invention with any of the carriers listed above.

Aerosol administration is also an alternative, requiring only that the immunogens be properly dispersed within the aerosol propellant. The use of a surfactant to properly disperse the immunogen may be required. Representative surfactants include the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. Typical propellants for such administration may include esters and similar chemicals but are by no means limited to these. A carrier, such as lecithin for intranasal delivery, may also be included.

The peptides and polypeptides of the invention may also be delivered with an adjuvant. Adjuvants include, but are not limited to, complete or incomplete Freund's adjuvant, Montanide ISA-51, Activation Gene-3 (LAO-3), aluminum phosphate, aluminum hydroxide, alum, and saponin. Adjuvant effects can also be obtained by injecting a variety of cytokines along with the immunogens of the invention. These cytokines include, but are not limited to IL-1, IL-2, IL-7, IL-12, and GM-CSF.

The peptides and polypeptides of the invention can also be added to professional antigen presenting cells such as dendritic cells that have been prepared ex vivo. The preparation of DC and loading with peptides at various concentrations using standard methods that are well known in the art. The peptide-pulsed dendrilic cells can then be administered either intravenously, subcutaneously, or intradermally, and the immunization may also include cytokines such as IL-2 or IL-12.

The present invention is also directed to a vaccine in which an immunogen of the present invention is delivered or administered in the form of a polynucleotide encoding the a polypeptide or active fragment as disclosed herein, whereby the peptide or polypeptide or active fragment is produced in vivo. The polynucleotide may be included in a suitable expression vector and combined with a pharmaceutically acceptable carrier. For example, the peptides or polypeptides could be expressed in plasmid DNA and nonreplicative viral vectors such as vaccinia, fowlpox, Venezuelan equine encephalitis virus, adenovirus, or other RNA or DNA viruses. These examples are meant to be illustrative only and should not be viewed as self-limiting. A wide variety of other vectors available and are apparent to those skilled in the art.

Regardless of the nature of the composition given, additional therapeutic agents may also accompany the immunogens of the present invention. Thus, for purposes of treating tumors, compositions containing the immunogens disclosed herein may, in addition, contain other antitumor pharmaceuticals. The use of such compositions with multiple active ingredients is left to the discretion of the clinician.

In addition, the immunogens of the present invention can be used to stimulate the production of antibodies for use in passive immunotherapy, for use as diagnostic reagents, and for use as reagents in other processes such as affinity chromatography.

The present invention also relates to antibodies that react with immunogens, such as a polypeptide comprising one or more of the epitopic peptides of SEQ ID NO: 1-53 as disclosed herein. Active fragments of such antibodies are also specifically contemplated. Such antibodies, and active fragments of such antibodies, for example, and Fab structure, may react with, including where it is highly selective or specific for, an immunogenic structure comprising 2, 3, 4 or more of the epitopic peptides of the invention.

With the advent of methods of molecular biology and recombinant technology, it is now possible for the artisan or ordinary skill to produce antibody molecules by recombinant means and thereby generate gene sequences that code for specific amino acid sequences found in the polypeptide structure of the antibodies.

Regardless of the source of the antibodies or nanobodies, or how the artisan of ordinary skill chooses to produce such antibodies or nanobodies, including recombinantly constructed or synthesized, in vitro or in vivo, by using transgenic animals, such as cows, goats and sheep, or by using cell cultures in bioreactors, or by direct chemical synthesis employing no living organisms at any stage of the process, all antibodies and nanobodies have regions capable of interacting with a structurally complementary antigenic target. The regions interacting with the target are referred to as "variable" or "V" regions and are characterized by differences in amino acid sequence from antibodies of different antigenic specificity.

The antibodies disclosed according to the invention may also be wholly synthetic, wherein the polypeptide chains of the antibodies are synthesized and, possibly, optimized for binding to the polypeptides disclosed herein as being receptors. Such antibodies may be chimeric or humanized antibodies and may be fully tetrameric in structure, or may be dimeric and comprise only a single heavy and a single light chain. Such antibodies may also include fragments, such as Fab and F(ab$_2$)' fragments, capable of reacting with and binding to any of the polypeptides disclosed herein as being receptors.

A further embodiment of the present invention relates to a method for inducing a CTL response in a subject comprising administering to subjects that express HLA A1, A2, A3 or A24 supertype antigens an effective (i.e., CTL-stimulating amount) of an immunogen of the invention that does not comprise the entire protein expressing the epitopic peptides disclosed herein (i.e., one that comprises less than the entire protein where the protein is a naturally occurring polypeptide) in an amount sufficient to induce a CTL response to tumor cells expressing at least HLA-A1 or HLA-A2, or HLA-A24 as the case may be, thereby eliciting a cellular response against said tumor cells.

A still further embodiment of the present invention relates to a method for inducing a CTL response in a subject, wherein the immunogen is in the form of a polynucleotide. In one non-limiting example, the method comprises administering to subjects that express HLA-A2 or HLA-A24 at least one CTL epitope, wherein said epitope or epitopes are selected from a group comprising the peptides disclosed according to the invention, and are coded within a polynucleotide sequence that does not comprise the entire protein coding region, in an amount sufficient to induce a CTL response to tumor cells expressing HLA-A2 or HLA-A24.

While the examples are provided below to illustrate the invention, it is to be understood that these methods and examples in no way limit the invention to the embodiments described herein and that other embodiments and uses will no doubt suggest themselves to those skilled in the art. All publications, patents, and patent applications cited herein are hereby incorporated by reference, as are the references cited therein. It is also to be understood that throughout this disclosure where the singular is used, the plural may be inferred and vice versa and use of either is not to be considered limiting.

EXAMPLE

Ovarian, pancreatic, lung, colon cancer cell lines were grown in complete medium. Cell lysates were prepared from cancer cells either treated with cisplatin drug or untreated and MHC/peptide complexes were isolated by immunoaffinity chromatography using MHC molecule specific antibodies The peptides purified from the MHC molecules were fractionated using C-18 reversed phase (RP) column (4.6 mm diameter×150 mm length) using an offline HPLC (Dionex, Sunnyvale, Calif.). The peptide containing fractions were collected and dried to 6 µL under vacuum for LC/MS/MS analysis.

Mass spectrometry experiments were carried out using LTQ (Thermo) and Orbitrap instruments interfaced with nano ultimate HPLC (Dionex). RP-HPLC purified peptide fractions were injected individually into the LC-MS/MS system to identify the sequences of the peptides. The peptides were analyzed using a Data-Dependent method. The acquired spectra data were searched against Swissprot protein database using Proteome Discoverer (Thermo) to interpret data and derive peptide sequences.

Synthetic peptides were made and subjected to LC-MS/MS analysis under identical experimental conditions as described above and their sequences were confirmed based on their MS/MS data. Candidate peptide sequences were confirmed by comparison of their MS/MS spectra with that of their synthetic analogs.

Heparinized blood from healthy HLA-A2+ donors was purchased from Research Blood Components, LLC (Brighton, Mass.). Peripheral blood mononuclear cells (PBMC) were purified using differential centrifugation following standard methods. PBMC were used to generate peptide specific CTL as described previously (Shetty, et al. J Proteomics. 2012 Jun. 18; 75(11):3270-90).

Human HLA-A2 and HLA-A24 transgenic mice were obtained from Taconic. Individual and peptide pools mixed with montanide 51 adjuvant and used for immunization. After prime and 2 boost immunizations, the spleen cells were harvested and assessed for peptide and tumor specific CTL responses.

Antigen stimulated interferon-γ (IFN-γ) release as a measure of CTL activation was assayed using an ELISPOT assay kit (BD-Pharmingen, San Jose, Calif.) according to the manufacturer's instructions. Results are presented as the number of interferon-γ producing cells per 1E6 PBMCs or splenocytes. Each assay was performed with PBMC from at least three different healthy donors or 3 mice per group. Error bars represent SEM of experimental replicates.

Fifty three epitopes including HLA-A2, A24, specific motifs were identified (Table 1) and several HLA-A2 and A24 specific epitopes were selected for in vitro (Seq ID: 1-3) and in vivo (Seq ID: HLA-A2: 4-7, HLA-A24: 8-13) CTL characterization studies. Synthetic peptides were made and used for CTL analysis.

Functional Characterization of Cancer Specific T Cell Epitopes:

Peptides Seq ID: 1-3 (STR, RLA, RVA) were selected to assess the CTL activation potential against ovarian, breast and cisplatin treated ovarian cancer cells (Shetty, et al. J Proteomics. 2012 Jun. 18; 75(11):3270-90). PBMCs from healthy HLA-A2+ donors were stimulated in vitro with synthetic peptides corresponding to each of the cancer epitopes. These cells were analyzed in an IFNγ ELISpot assay using T2 cells loaded with the synthetic peptides, normal cells suspensions obtained from HLA-A2+ healthy liver tissues and HLA-A2+ ovarian (OVCAR3, SKOV3, SKOV3+C-cisplatin treated) and breast (MDA) cancer cells. As shown in FIG. 1, CTLs generated against all 9 cancer epitopes recognized peptide loaded T2 cells to demonstrate antigen specificity. In addition, CTLs recognized both ovarian and breast cancer cells and cisplatin treated (resistant) cancer cells and not normal liver cells indicating these epitopes are endogenously presented on these cancer cells and not on non-malignant normal cells.

In addition to in vitro CTL characterization, peptides Seq ID: 4 (LLDEQ), 5 (KTL), 6 (LLDEK), 7 (FAN), (ILA-A2 specific) 8-13(HLA-A24 specific—IYK, AYL, LLY, AYV, IFG, MYF) were assessed for CTL activation in vivo in human HLA transgenic mouse model. Splenocytes obtained from immunized mice were tested for CTL activity against peptide loaded T2, normal lung (N Lung) or pancreas (N Panc) cells and various lung (H522, HTB177, 5865, 5944), colon (227, 228) and pancreatic (Panc1, MP2-Miapaca 2) tumor cells. As shown in FIG. 2A, HLA-A2 peptide specific CTLs recognize HLA-A2+ lung, colon and pancreatic cancer cells in addition to individual peptide loaded 12 and normal lung or pancreas cells indicating that the CTLs are peptide specific and capable of recognizing endogenously presented epitopes on the cancer cells. FIG. 2B represents the CTL activation for HLA-A24 specific epitopes in HLA-A24 transgenic mice. Nine HLA-A24 epitopes were pooled for immunization and the data (FIG. 2C) indicates that pooled immunization generates individual peptides specific CTL response as demonstrated by peptide loaded T2 response and a robust HLA-A24+ lung and pancreatic tumor specific response.

TABLE 1

Parent Sequence Identification and Parent SwissProt ID Number for Peptides 1-53

| SEQ ID No | Peptide sequence | Parent Sequence Identification | SwissProt ID No |
|---|---|---|---|
| 1 | STRKDYPAAK | Myc proto-oncogene protein | P01106 |
| 2 | RLAADDFRV | Keratin, type I cytoskeletal 18 | P05783 |
| 3 | RVAPRSGLAAK | Deoxyuridine 5'-triphosphate nucleotidohydrolase, mitochondrial | P33316 |
| 4 | LLDEQQVNV | ID1 Isoform | P41134-1 |
| 5 | KTLEGEFSV | YY1 Transcriptional repressor protein | P25490 |
| 6 | LLDEKEPEV | NBPF3 Isoform 1 | Q9H094-1 |
| 7 | FANYIDKV | Vimentin | P08670 |
| 8 | IYKAPSENW | DNA (cytosine-5)-methyltransferase 1 | P26358 |
| 9 | AYLDKSPQF | ATP-dependent RNA helicase DHX29 | Q7Z478 |
| 10 | LLYQEGAKMAV | Junction plakoglobin | P14923 |
| 11 | AYVEKVERL | AMOTL2 Isoform 2 of Angiomotin-like protein 2 | Q9Y2J4 |
| 12 | IFGVIIDTF | ITPR2 Isoform Long of Inositol 1,4,5-trisphosphate receptor type 2 | Q14571 |
| 13 | MYFQTHDQIGM | UPF1 Isoform 1 of Regulator of nonsense transcripts 1 | Q92900 |
| 14 | SLDVSAPKV | Protein AHNAK2 | Q8IVF2 |

TABLE 1 -continued

Parent Sequence Identification and Parent SwissProt ID Number for Peptides 1-53

| SEQ ID No | Peptide sequence | Parent Sequence Identification | SwissProt ID No |
|---|---|---|---|
| 15 | FLFEDFSKA | Transmembrane protein 97 | Q5BJF2 |
| 16 | YATPIIMDM | DCBD2_HUMAN Discoidin, CUB and LCCL domain-containing protein 2 | Q96PD2 |
| 17 | KLKEEIDLLNR | PAWR_HUMAN PRKC apoptosis WT1 regulator protein | Q96IZ0 |
| 18 | AIIEYMPLL | Serine/threonine-protein phosphatase 2A 65 kDa regulatory subunit A alpha isoform | P30153 |
| 19 | GVMSPPQGLMT | B-cell CLL/lymphoma 9-like protein | Q86UU0 |
| 20 | LMGPPPQQNL | B-cell CLL/lymphoma 9-like protein2 | Q86UU0 |
| 21 | TLMEALHYM | Exportin-1 | Q14980 |
| 22 | TLSDIMVSL | Testis-expressed sequence 10 protein | Q9NXF1 |
| 23 | YQPYNMQNL | Hepatocyte growth factor-regulated tyrosine kinase substrate | O14964 |
| 24 | ALDSTNVEA | Ras-related protein Rab-11A | P62491 |
| 25 | FAEVKNQEV | Homeobox protein cut-like 1 | P39880 |
| 26 | NLDNPIQTV | Nodal modulator 1 | Q15155 |
| 27 | RLDSTGVNV | Protein FAM72A | Q5TYM5 |
| 28 | YIDDTLTMV | GGNB2_HUMAN Gametogenetin-binding protein 2 | Q9H3C7 |
| 29 | YATPIIMDM | DCBD2_HUMAN Discoidin, CUB and LCCL domain-containing protein 2_b | Q96PD2 |
| 30 | DMYLAPHV | CSN1_HUMAN COP9 signalosome complex subunit 1 | Q13098 |
| 31 | MMEVKDPNM | RBBP6_HUMAN Retinoblastoma-binding protein 6 | Q7Z6E9 |
| 32 | VVLPAPPAV | RANBP9 Isoform 1 of Ran-binding protein 9 | Q96S59 |
| 33 | DAYVGYMTI | FBX11_HUMAN F-box only protein 11 | Q86XK2 |
| 34 | KLKDGNRISL | M3K9_HUMAN Mitogen-activated protein kinase kinase kinase 9 | P80192 |
| 35 | RVLNKLGGVK | Copper transport protein ATOX1 | O00244 |
| 36 | RILANWLKVK | 80 kDa MCM3-associated protein | O60318 |
| 37 | NTIPEVHKK | Antizyme inhibitor 1 | O14977 |
| 38 | RIMHIQPPK | Mediator of RNA polymerase II transcription subunit 19 | A0JLT2 |
| 39 | ILYDHAHVK | Ornithine decarboxylase | P11926 |
| 40 | GTIGHVAHGK | Eukaryotic translation initiation factor 2 subunit 3 | P41091 |
| 41 | ATSVITIVK | Transcription factor MafG | O15525 |
| 42 | VTAPPARNR | CGG triplet repeat-binding protein 1 | Q9UFW8 |
| 43 | RVFHPAFTK | Growth hormone-inducible transmembrane protein | Q9H3K2 |
| 44 | RLAHASIMK | Protein OSCP1 | Q8WVF1 |
| 45 | PVTVKMQLRRP | Proto-oncogene c-Rel | Q04864 |
| 46 | EYMLQNHVF | Importin-7 OS | O95373 |

TABLE 1 -continued

Parent Sequence Identification and Parent SwissProt ID Number for Peptides 1-53

| SEQ ID No | Peptide sequence | Parent Sequence Identification | SwissProt ID No |
|---|---|---|---|
| 47 | FYQNNKDF | Eukaryotic translation initiation factor 3 subunit M | Q7L2H7 |
| 48 | GYEPPVQESV | 40S ribosomal protein S3a | P61247 |
| 49 | IYPEVVHMF | Serine/threonine-protein phosphatase 2A | Q13362 |
| 50 | LYKACSVIFP | Squalene monooxygenase | Q14534 |
| 51 | RYLMDPDTF | Probable DNA | Q9UH17 |
| 52 | SYVVAMETF | DNA damage-binding protein 1 | Q16531 |
| 53 | YYMKDLPTSF | Phosphatidylinositol 4-kinase alpha | P42356 |
| 1 | STRKDYPAAK | Myc proto-oncogene protein | P01106 |
| 2 | RLAADDFRV | Keratin, type I cytoskeletal 18 | P05783 |
| 3 | RVAPRSGLAAK | Deoxyuridine 5'-triphosphate nucleotidohydrolase, mitochondrial | P33316 |
| 4 | LLDEQQVNV | ID1 Isoform | P41134-1 |
| 5 | KTLEGEFSV | YY1 Transcriptional repressor protein | P25490 |
| 6 | LLDEKEPEV | NBPF3 Isoform 1 | Q9H094-1 |
| 7 | FANYIDKV | Vimentin | P08670 |
| 8 | IYKAPSENW | DNA (cytosine-5)-methyltransferase 1 | P26358 |
| 9 | AYLDKSPQF | ATP-dependent RNA helicase DHX29 | Q7Z478 |
| 10 | LLYQEGAKMAV | Junction plakoglobin | P14923 |
| 11 | AYVEKVERL | AMOTL2 Isoform 2 of Angiomotin-like protein 2 | Q9Y2J4 |
| 12 | IFGVIIDTF | ITPR2 Isoform Long of Inositol 1,4,5-trisphosphate receptor type 2 | Q14571 |
| 13 | MYFQTHDQIGM | UPF1 Isoform 1 of Regulator of nonsense transcripts 1 | Q92900 |
| 14 | SLDVSAPKV | Protein AHNAK2 | Q8IVF2 |
| 15 | FLFEDFSKA | Transmembrane protein 97 | Q5B1F2 |
| 16 | YATPIIMDM | DCBD2_HUMAN Discoidin, CUB and LCCL domain-containing protein 2 | Q96PD2 |
| 17 | KLKEEIDLLNR | PAWR_HUMAN PRKC apoptosis WT1 regulator protein | Q96IZ0 |
| 18 | AIIEYMPLL | Serine/threonine-protein phosphatase 2A 65 kDa regulatory subunit A alpha isoform | P30153 |
| 19 | GVMSPPQGLMT | B-cell CLL/lymphoma 9-like protein | Q86UU0 |
| 20 | LMGPPPQQNL | B-cell CLL/lymphoma 9-like protein2 | Q86UU0 |
| 21 | TLMEALHYM | Exportin-1 | O14980 |
| 22 | TLSDIMVSL | Testis-expressed sequence 10 protein | Q9NXF1 |
| 23 | YQPYNMQNL | Hepatocyte growth factor-regulated tyrosine kinase substrate | O14964 |
| 24 | ALDSTNVEA | Ras-related protein Rab-11A | P62491 |
| 25 | FAEVKNQEV | Homeobox protein cut-like 1 | P39880 |
| 26 | NLDNPIQTV | Nodal modulator 1 | Q15155 |

TABLE 1 -continued

Parent Sequence Identification and Parent SwissProt ID Number for Peptides 1-53

| SEQ ID No | Peptide sequence | Parent Sequence Identification | SwissProt ID No |
|---|---|---|---|
| 27 | RLDSTGVNV | Protein FAM72A | Q5TYM5 |
| 28 | YIDDTLTMV | GGNB2_HUMAN Gametogenetin-binding protein 2 | Q9H3C7 |
| 29 | YATPIIMDM | DCBD2_HUMAN Discoidin, CUB and LCCL domain-containing protein 2_b | Q96PD2 |
| 30 | DMYLAPHV | CSN1_HUMAN COP9 signalosome complex subunit 1 | Q13098 |
| 31 | MMEVKDPNM | RBBP6_HUMAN Retinoblastoma-binding protein 6 | Q7Z6E9 |
| 32 | VVLPAPPAV | RANBP9 Isoform 1 of Ran-binding protein 9 | Q96S59 |
| 33 | DAYVGYMTI | FBX11_HUMAN F-box only protein 11 | Q86XK2 |
| 34 | KLKDGNRISL | M3K9_HUMAN Mitogen-activated protein kinase kinase kinase 9 | P80192 |
| 35 | RVLNKLGGVK | Copper transport protein ATOX1 | O00244 |
| 36 | RILANWLKVK | 80 kDa MCM3-associated protein | O60318 |
| 37 | NTIPEVHKK | Antizyme inhibitor 1 | O14977 |
| 38 | RLMHIQPPK | Mediator of RNA polymerase II transcription subunit 19 | A0JLT2 |
| 39 | ILYDHAHVK | Ornithine decarboxylase | P11926 |
| 40 | GTIGHVAHGK | Eukaryotic translation initiation factor 2 subunit 3 | P41091 |
| 41 | ATSVITIVK | Transcription factor MafG | O15525 |
| 42 | VTAPPARNR | CGG triplet repeat-binding protein 1 | Q9UFW8 |
| 43 | RVFHPAFTK | Growth hormone-inducible transmembrane protein | Q9H3K2 |
| 44 | RLAHASIMK | Protein OSCP1 | Q8WVF1 |
| 45 | PVTVKMQLRRP | Proto-oncogene c-Rel | Q04864 |
| 46 | EYMLQNHVF | Importin-7 OS | O95373 |
| 47 | FYQNNKDF | Eukaryotic translation initiation factor 3 subunit M | Q7L2H7 |
| 48 | GYEPPVQESV | 40S ribosomal protein S3a | P61247 |
| 49 | IYPEVVHMF | Serine/threonine-protein phosphatase 2A | Q13362 |
| 50 | LYKACSVIFP | Squalene monooxygenase | Q14534 |
| 51 | RYLMDPDTF | Probable DNA | Q9UH17 |
| 52 | SYVVAMETF | DNA damage-binding protein 1 | Q16531 |
| 53 | YMKDLPTSF | Phosphatidylinositol 4-kinase alpha | P42356 |

The invention claimed is:

1. A method for treating tumor cells in a subject comprising:
   (a) eliciting a CTL response against tumor cells presenting at least one epitopic peptide from a group of peptides consisting of SEQ ID NOS: 1 through 3 and SEQ ID NOS: 5 through 53 by administration of a sufficient amount of a composition containing at least one peptide from the group and a stabilizing agent; or
   (b) stimulating an immune response in an immunologically competent animal, said composition consisting of at least one of SEQ ID NOS: 1 through 3 and SEQ ID NOS: 5 through 53 and a stabilizing agent capable of facilitating an immune response thereof.

2. The method of claim 1, wherein said composition further comprises an adjuvant, optionally wherein said adjuvant is selected from the group consisting of complete Freund's adjuvant, incomplete Freund's adjuvant, Montanide ISA-51, LAG-3, aluminum phosphate, aluminum hydroxide, alum, and saponin.

3. The method of claim 1, wherein said composition further comprises a cytokine, optionally wherein said cytokine is selected from the group consisting of IL-1, IL-2, IL-7, IL-12, IL-15, TNF, SCF and GM-CSF.

4. The method of claim 1, wherein said composition further comprises a vehicle, optionally wherein said vehicle is selected from the group consisting of a liposome, nanoparticles, an immunostimulating complex (ISCOM), and slow-releasing particles.

5. The method of claim 4, wherein said liposome comprises an emulsion, a foam, a micelle, an insoluble monolayer, a liquid crystal, phospholipid dispersion, or a lamellar layer.

6. The method of claim 1 (a), wherein said tumor cells are part of a carcinoma.

7. The method of claim 6, wherein said tumor cells are part of an ovarian carcinoma.

8. A method for treating tumor cells in a subject comprising:
   (a) eliciting a CTL response against tumor cells presenting at least one epitopic peptide from a group of peptides consisting of SEQ ID NOS: 1 through 3 and SEQ ID NOS: 5 through 53 by administration of a sufficient amount of a composition containing at least one peptide from the group linked through a non-conventional peptide bond to an additional peptide sequence and a stabilizing agent; or
   (b) stimulating an immune response in an immunologically competent animal, said composition consisting of at least one of SEQ ID NOS: 1 through 3 and SEQ ID NOS: 5 through 53 and a stabilizing agent capable of facilitating an immune response thereof.

* * * * *

SEQUENCE LISTING

<160> NUMBER OF SEQ ID NOS: 53

<210> SEQ ID NO 1
<211> LENGTH: 10
<212> TYPE: PRT
<213> ORGANISM: Homo sapiens

<400> SEQUENCE: 1

```
Ser Thr Arg Lys Asp Tyr Pro Ala Ala Lys
1               5                   10
```

```
<210> SEQ ID NO 2
<211> LENGTH: 9
<212> TYPE: PRT
<213> ORGANISM: Homo sapiens

<400> SEQUENCE: 2

Arg Leu Ala Ala Asp Asp Phe Arg Val
1               5
```

```
<210> SEQ ID NO 3
<211> LENGTH: 11
<212> TYPE: PRT
<213> ORGANISM: Homo sapiens

<400> SEQUENCE: 3

Arg Val Ala Pro Arg Ser Gly Leu Ala Ala Lys
1               5                   10
```

```
<210> SEQ ID NO 4
<211> LENGTH: 9
<212> TYPE: PRT
<213> ORGANISM: Homo sapiens

<400> SEQUENCE: 4

Leu Leu Asp Glu Gln Gln Val Asn Val
1               5
```

```
<210> SEQ ID NO 5
<211> LENGTH: 9
<212> TYPE: PRT
<213> ORGANISM: Homo sapiens

<400> SEQUENCE: 5

Lys Thr Leu Glu Gly Glu Phe Ser Val
1               5
```

```
<210> SEQ ID NO 6
<211> LENGTH: 9
<212> TYPE: PRT
<213> ORGANISM: Homo sapiens

<400> SEQUENCE: 6

Leu Leu Asp Glu Lys Glu Pro Glu Val
1               5
```

```
<210> SEQ ID NO 7
<211> LENGTH: 8
<212> TYPE: PRT
<213> ORGANISM: Homo sapiens

<400> SEQUENCE: 7

Phe Ala Asn Tyr Ile Asp Lys Val
1               5
```

```
<210> SEQ ID NO 8
<211> LENGTH: 9
<212> TYPE: PRT
<213> ORGANISM: Homo sapiens

<400> SEQUENCE: 8

Ile Tyr Lys Ala Pro Ser Glu Asn Trp
1               5
```

<210> SEQ ID NO 9
<211> LENGTH: 9
<212> TYPE: PRT
<213> ORGANISM: Homo sapiens

<400> SEQUENCE: 9

Ala Tyr Leu Asp Lys Ser Pro Gln Phe
1               5

<210> SEQ ID NO 10
<211> LENGTH: 11
<212> TYPE: PRT
<213> ORGANISM: Homo sapiens

<400> SEQUENCE: 10

Leu Leu Tyr Gln Glu Gly Ala Lys Met Ala Val
1               5                   10

<210> SEQ ID NO 11
<211> LENGTH: 9
<212> TYPE: PRT
<213> ORGANISM: Homo sapiens

<400> SEQUENCE: 11

Ala Tyr Val Glu Lys Val Glu Arg Leu
1               5

<210> SEQ ID NO 12
<211> LENGTH: 9
<212> TYPE: PRT
<213> ORGANISM: Homo sapiens

<400> SEQUENCE: 12

Ile Phe Gly Val Ile Ile Asp Thr Phe
1               5

<210> SEQ ID NO 13
<211> LENGTH: 11
<212> TYPE: PRT
<213> ORGANISM: Homo sapiens

<400> SEQUENCE: 13

Met Tyr Phe Gln Thr His Asp Gln Ile Gly Met
1               5                   10

<210> SEQ ID NO 14
<211> LENGTH: 9
<212> TYPE: PRT
<213> ORGANISM: Homo sapiens

<400> SEQUENCE: 14

Ser Leu Asp Val Ser Ala Pro Lys Val
1               5

<210> SEQ ID NO 15
<211> LENGTH: 9
<212> TYPE: PRT
<213> ORGANISM: Homo sapiens

<400> SEQUENCE: 15

Phe Leu Phe Glu Asp Phe Ser Lys Ala
1               5

```
<210> SEQ ID NO 16
<211> LENGTH: 9
<212> TYPE: PRT
<213> ORGANISM: Homo sapiens

<400> SEQUENCE: 16

Tyr Ala Thr Pro Ile Ile Met Asp Met
1               5

<210> SEQ ID NO 17
<211> LENGTH: 11
<212> TYPE: PRT
<213> ORGANISM: Homo sapiens

<400> SEQUENCE: 17

Lys Leu Lys Glu Glu Ile Asp Leu Leu Asn Arg
1               5                   10

<210> SEQ ID NO 18
<211> LENGTH: 9
<212> TYPE: PRT
<213> ORGANISM: Homo sapiens

<400> SEQUENCE: 18

Ala Ile Ile Glu Tyr Met Pro Leu Leu
1               5

<210> SEQ ID NO 19
<211> LENGTH: 11
<212> TYPE: PRT
<213> ORGANISM: Homo sapiens

<400> SEQUENCE: 19

Gly Val Met Ser Pro Pro Gln Gly Leu Met Thr
1               5                   10

<210> SEQ ID NO 20
<211> LENGTH: 10
<212> TYPE: PRT
<213> ORGANISM: Homo sapiens

<400> SEQUENCE: 20

Leu Met Gly Pro Pro Pro Gln Gln Asn Leu
1               5                   10

<210> SEQ ID NO 21
<211> LENGTH: 9
<212> TYPE: PRT
<213> ORGANISM: Homo sapiens

<400> SEQUENCE: 21

Thr Leu Met Glu Ala Leu His Tyr Met
1               5

<210> SEQ ID NO 22
<211> LENGTH: 9
<212> TYPE: PRT
<213> ORGANISM: Homo sapiens

<400> SEQUENCE: 22

Thr Leu Ser Asp Ile Met Val Ser Leu
1               5

<210> SEQ ID NO 23
<211> LENGTH: 9
```

```
<212> TYPE: PRT
<213> ORGANISM: Homo sapiens

<400> SEQUENCE: 23

Tyr Gln Pro Tyr Asn Met Gln Asn Leu
1               5

<210> SEQ ID NO 24
<211> LENGTH: 9
<212> TYPE: PRT
<213> ORGANISM: Homo sapiens

<400> SEQUENCE: 24

Ala Leu Asp Ser Thr Asn Val Glu Ala
1               5

<210> SEQ ID NO 25
<211> LENGTH: 9
<212> TYPE: PRT
<213> ORGANISM: Homo sapiens

<400> SEQUENCE: 25

Phe Ala Glu Val Lys Asn Gln Glu Val
1               5

<210> SEQ ID NO 26
<211> LENGTH: 9
<212> TYPE: PRT
<213> ORGANISM: Homo sapiens

<400> SEQUENCE: 26

Asn Leu Asp Asn Pro Ile Gln Thr Val
1               5

<210> SEQ ID NO 27
<211> LENGTH: 9
<212> TYPE: PRT
<213> ORGANISM: Homo sapiens

<400> SEQUENCE: 27

Arg Leu Asp Ser Thr Gly Val Asn Val
1               5

<210> SEQ ID NO 28
<211> LENGTH: 9
<212> TYPE: PRT
<213> ORGANISM: Homo sapiens

<400> SEQUENCE: 28

Tyr Ile Asp Asp Thr Leu Thr Met Val
1               5

<210> SEQ ID NO 29
<211> LENGTH: 9
<212> TYPE: PRT
<213> ORGANISM: Homo sapiens

<400> SEQUENCE: 29

Tyr Ala Thr Pro Ile Ile Met Asp Met
1               5

<210> SEQ ID NO 30
<211> LENGTH: 8
<212> TYPE: PRT
<213> ORGANISM: Homo sapiens
```

-continued

<400> SEQUENCE: 30

Asp Met Tyr Leu Ala Pro His Val
1               5

<210> SEQ ID NO 31
<211> LENGTH: 9
<212> TYPE: PRT
<213> ORGANISM: Homo sapiens

<400> SEQUENCE: 31

Met Met Glu Val Lys Asp Pro Asn Met
1               5

<210> SEQ ID NO 32
<211> LENGTH: 9
<212> TYPE: PRT
<213> ORGANISM: Homo sapiens

<400> SEQUENCE: 32

Val Val Leu Pro Ala Pro Pro Ala Val
1               5

<210> SEQ ID NO 33
<211> LENGTH: 9
<212> TYPE: PRT
<213> ORGANISM: Homo sapiens

<400> SEQUENCE: 33

Asp Ala Tyr Val Gly Tyr Met Thr Ile
1               5

<210> SEQ ID NO 34
<211> LENGTH: 10
<212> TYPE: PRT
<213> ORGANISM: Homo sapiens

<400> SEQUENCE: 34

Lys Leu Lys Asp Gly Asn Arg Ile Ser Leu
1               5                   10

<210> SEQ ID NO 35
<211> LENGTH: 10
<212> TYPE: PRT
<213> ORGANISM: Homo sapiens

<400> SEQUENCE: 35

Arg Val Leu Asn Lys Leu Gly Gly Val Lys
1               5                   10

<210> SEQ ID NO 36
<211> LENGTH: 10
<212> TYPE: PRT
<213> ORGANISM: Homo sapiens

<400> SEQUENCE: 36

Arg Ile Leu Ala Asn Trp Leu Lys Val Lys
1               5                   10

<210> SEQ ID NO 37
<211> LENGTH: 9
<212> TYPE: PRT
<213> ORGANISM: Homo sapiens

<400> SEQUENCE: 37

Asn Thr Ile Pro Glu Val His Lys Lys
1               5

<210> SEQ ID NO 38
<211> LENGTH: 9
<212> TYPE: PRT
<213> ORGANISM: Homo sapiens

<400> SEQUENCE: 38

Arg Leu Met His Ile Gln Pro Pro Lys
1               5

<210> SEQ ID NO 39
<211> LENGTH: 9
<212> TYPE: PRT
<213> ORGANISM: Homo sapiens

<400> SEQUENCE: 39

Ile Leu Tyr Asp His Ala His Val Lys
1               5

<210> SEQ ID NO 40
<211> LENGTH: 10
<212> TYPE: PRT
<213> ORGANISM: Homo sapiens

<400> SEQUENCE: 40

Gly Thr Ile Gly His Val Ala His Gly Lys
1               5                   10

<210> SEQ ID NO 41
<211> LENGTH: 9
<212> TYPE: PRT
<213> ORGANISM: Homo sapiens

<400> SEQUENCE: 41

Ala Thr Ser Val Ile Thr Ile Val Lys
1               5

<210> SEQ ID NO 42
<211> LENGTH: 9
<212> TYPE: PRT
<213> ORGANISM: Homo sapiens

<400> SEQUENCE: 42

Val Thr Ala Pro Pro Ala Arg Asn Arg
1               5

<210> SEQ ID NO 43
<211> LENGTH: 9
<212> TYPE: PRT
<213> ORGANISM: Homo sapiens

<400> SEQUENCE: 43

Arg Val Phe His Pro Ala Phe Thr Lys
1               5

<210> SEQ ID NO 44
<211> LENGTH: 9
<212> TYPE: PRT
<213> ORGANISM: Homo sapiens

<400> SEQUENCE: 44

Arg Leu Ala His Ala Ser Ile Met Lys

<210> SEQ ID NO 45
<211> LENGTH: 11
<212> TYPE: PRT
<213> ORGANISM: Homo sapiens

<400> SEQUENCE: 45

Pro Val Thr Val Lys Met Gln Leu Arg Arg Pro
1               5                   10

<210> SEQ ID NO 46
<211> LENGTH: 9
<212> TYPE: PRT
<213> ORGANISM: Homo sapiens

<400> SEQUENCE: 46

Glu Tyr Met Leu Gln Asn His Val Phe
1               5

<210> SEQ ID NO 47
<211> LENGTH: 8
<212> TYPE: PRT
<213> ORGANISM: Homo sapiens

<400> SEQUENCE: 47

Phe Tyr Gln Asn Asn Lys Asp Phe
1               5

<210> SEQ ID NO 48
<211> LENGTH: 10
<212> TYPE: PRT
<213> ORGANISM: Homo sapiens

<400> SEQUENCE: 48

Gly Tyr Glu Pro Pro Val Gln Glu Ser Val
1               5                   10

<210> SEQ ID NO 49
<211> LENGTH: 9
<212> TYPE: PRT
<213> ORGANISM: Homo sapiens

<400> SEQUENCE: 49

Ile Tyr Pro Glu Val Val His Met Phe
1               5

<210> SEQ ID NO 50
<211> LENGTH: 10
<212> TYPE: PRT
<213> ORGANISM: Homo sapiens

<400> SEQUENCE: 50

Leu Tyr Lys Ala Cys Ser Val Ile Phe Pro
1               5                   10

<210> SEQ ID NO 51
<211> LENGTH: 9
<212> TYPE: PRT
<213> ORGANISM: Homo sapiens

<400> SEQUENCE: 51

Arg Tyr Leu Met Asp Pro Asp Thr Phe
1               5

```
<210> SEQ ID NO 52
<211> LENGTH: 9
<212> TYPE: PRT
<213> ORGANISM: Homo sapiens

<400> SEQUENCE: 52

Ser Tyr Val Val Ala Met Glu Thr Phe
1               5

<210> SEQ ID NO 53
<211> LENGTH: 10
<212> TYPE: PRT
<213> ORGANISM: Homo sapiens

<400> SEQUENCE: 53

Tyr Tyr Met Lys Asp Leu Pro Thr Ser Phe
1               5                   10
```